United States Patent
Obana et al.

(10) Patent No.: US 6,867,164 B2
(45) Date of Patent: Mar. 15, 2005

(54) CATALYST FOR PRODUCTION OF ACETIC ACID OR ACETIC ACID AND ETHYL ACETATE, PROCESS FOR ITS PRODUCTION AND PROCESS FOR PRODUCTION OF ACETIC ACID OR ACETIC ACID AND ETHYL ACETATE USING IT

(75) Inventors: Yoshiaki Obana, Oita (JP); Hiroshi Uchida, Oita (JP); Ken-ichi Sano, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 96 days.

(21) Appl. No.: 10/244,428

(22) Filed: Sep. 17, 2002

(65) Prior Publication Data

US 2003/0092936 A1 May 15, 2003

Related U.S. Application Data

(62) Division of application No. 09/554,752, filed as application No. PCT/JP00/02203 on Apr. 5, 2000, now Pat. No. 6,552,220.
(60) Provisional application No. 60/160,004, filed on Oct. 18, 1999, and provisional application No. 60/134,847, filed on May 19, 1999.

(30) Foreign Application Priority Data

Apr. 14, 1999 (JP) ............................................ 11-106358
Sep. 9, 1999 (JP) ............................................ 11-255018

(51) Int. Cl.⁷ ........................ C07C 51/16; C07C 67/00; C07C 69/02; B01J 23/44
(52) U.S. Cl. ........................ 502/333; 562/538; 562/617; 562/519; 562/607; 560/231; 560/232; 560/239
(58) Field of Search ............................ 562/538, 617, 562/519, 607, 517; 560/239, 231, 232; 502/210, 333

(56) References Cited

U.S. PATENT DOCUMENTS 3,739,020 A    6/1973  McClain et al.
4,188,490 A  * 2/1980  Hinnenkamp et al. ...... 560/245
4,935,549 A  * 6/1990  Kamiguchi et al. ......... 562/548
5,162,578 A  * 11/1992 McCain, Jr. et al. ..... 562/512.2
5,321,156 A    6/1994  Behr et al.
5,330,955 A  * 7/1994  Wegman ..................... 502/210
5,334,751 A  * 8/1994  Lemanski et al. .......... 560/265
5,840,971 A  * 11/1998 Gubelmann-Bonneau ... 562/538
5,856,263 A    1/1999  Bhasin et al.

FOREIGN PATENT DOCUMENTS

| DE | 3135946 A | 3/1983 |
|---|---|---|
| FR | 2720741 A | 12/1995 |
| JP | 48-19292 | 6/1973 |
| JP | 57-102835 A | 6/1982 |
| JP | 4-300851 A | 10/1992 |
| WO | WO 96/25379 A | 8/1996 |
| WO | WO 97/44130 A | 11/1997 |
| WO | WO 98/37966 A | 9/1998 |

* cited by examiner

Primary Examiner—Cecilia J. Tsang
Assistant Examiner—Taylor V. Oh
(74) Attorney, Agent, or Firm—Sughrue Mion, PLLC

(57) ABSTRACT

An acetic acid production catalyst that contains (b) at least one element selected from the group consisting of Group 14 elements, Group 15 elements and Group 16 elements of the Periodic Table and/or (c) at least one element selected from the group consisting of Group 6 elements, Group 7 elements, Group 8 elements, Group 9 elements, Group 10 elements, Group 11 elements and Group 12 elements of the Periodic Table, added to a palladium-loaded catalyst, as well as an acetic acid and ethyl acetate production catalyst that contains (b) at least one compound selected from the group consisting of inorganic acids and salts thereof and/or (c) at least one element selected from the group consisting of Group 14 elements, Group 15 elements and Group 16 elements of the Periodic Table and/or (d) at least one element selected from the group consisting of Group 6 elements, Group 7 elements, Group 8 elements, Group 9 elements, Group 10 elements, Group 11 elements and Group 12 elements of the Periodic Table, added to palladium.

8 Claims, No Drawings

CATALYST FOR PRODUCTION OF ACETIC ACID OR ACETIC ACID AND ETHYL ACETATE, PROCESS FOR ITS PRODUCTION AND PROCESS FOR PRODUCTION OF ACETIC ACID OR ACETIC ACID AND ETHYL ACETATE USING IT

CROSS REFERENCE TO RELATED APPLICATIONS

This is a divisional of Application Ser. No. 09/554,752, filed May 19, 2000 now U.S. Pat. No. 6,552,220, the Disclosure of which is incorporated herein by reference, which was the National Stage of International Application No. PCT/JP00/02203, filed Apr. 5, 2000, which claims benefit of Provisional Application No. 60/134,847, filed May 19, 1999 and Provisional Application No. 60/160,004, filed Oct. 18, 1999.

TECHNICAL FIELD

The present invention relates to a catalyst for production of acetic acid or acetic acid and ethyl acetate from ethanol and oxygen, to a process for its production and to a process for production of acetic acid or acetic acid and ethyl acetate using the catalyst.

BACKGROUND ART

Processes for industrial production of acetic acid that have been realized include a process using oxidation of acetaldehyde, a process using a reaction of methanol and carbon monoxide and a process using oxidation of lower paraffins. Processes for industrial production of ethyl acetate that have been realized include an esterification reaction of ethanol and acetic acid, and a dimerization reaction of acetaldehyde.

In recent years, various production processes for acetic acid using ethanol as the starting material have been studied as an alternative.

An example of a process for obtaining acetic acid from ethanol in a single stage which employs copper oxide as the main catalyst in combination with zinc oxide, chromium oxide and (chromium oxide-manganese oxide) (Japanese Unexamined Patent Publication No. 57-102835) has been disclosed. However, this process has been difficult to apply on an industrially practical scale because the reaction temperature is high at 260–360° C., and the acetic acid selectivity is not sufficient.

Oxidation processes with catalysts of platinum group metals, particularly palladium, have also been disclosed. For example, acetic acid can be obtained by reacting a catalyst of metallic palladium or palladium loaded on a carrier such as silica or alumina (Japanese Examined Patent Publication No. 48-19292, Brazil Patent BR-9104562) with ethanol and oxygen. Palladium catalysts offer the advantage of a relatively low reaction temperature of 100–200° C. However, these processes have all had the drawback of abundant by-products such as acetaldehyde and carbon dioxide, which have lowered the yield of the target acetic acid.

Processes using metallic palladium-loaded catalysts have been disclosed as processes for obtaining ethyl acetate from ethanol by a single stage. For example, according to Kunugi and Matsuura et al. (Kogyo Kagaku Zasshi, Vol. 71, No. 9, p. 1517 (1968)), ethyl acetate is obtained from ethanol and oxygen in the vapor phase using a catalyst of metallic palladium loaded on a carrier of active carbon, γ-alumina or the like. Ethyl acetate is also obtained from ethanol and oxygen using a metallic palladium/γ-alumina catalyst (Brazil Patent BR-8901776). However, these processes have had the disadvantage of a low conversion rate of ethanol and abundant by-products such as acetaldehyde, methane and carbon dioxide, which have lowered yields of the target ethyl acetate.

There has also been disclosed a catalyst including a palladium component and crystalline titanium pyrophosphate represented by ($TiP_2O_7$) (Japanese Unexamined Patent Publication No. 4-300851). Here, improvement in ethyl acetate production activity has been reported by use of this binary catalyst having palladium and titanium pyrophosphate as essential components, but even this process has low ethyl acetate production activity and selectivity, and is inadequate in practical terms on an industrial scale.

On the other hand, processes employing palladium as the catalyst allow acetic acid and/or ethyl acetate to be obtained from ethanol and oxygen under relatively mild reaction conditions. Notwithstanding, for industrial scale production, a catalyst that is capable of catalyzing the reaction with even higher activity and higher selectivity is strongly desired.

DISCLOSURE OF INVENTION

It is an object of the present invention to provide a catalyst to be used for production of acetic acid or acetic acid and ethyl acetate from ethanol and oxygen, a process for its production, and a process for production of acetic acid or acetic acid and ethyl acetate using the catalyst.

In order to achieve this object, the present inventors have conducted diligent research aimed at further increasing catalyst performance in a process for producing acetic acid or acetic acid and ethyl acetate from ethanol and oxygen using a palladium catalyst, and as a result we have completed the present invention upon finding a catalyst with very low carbon dioxide selectivity, high activity and a long service life.

Specifically, the invention (I) is a catalyst for production of acetic acid, which is a catalyst used in a process for production of acetic acid by reaction of ethanol and oxygen that comprises (a) metallic palladium and (b) at least one element selected from the group consisting of Group 14 elements, Group 15 elements and Group 16 elements of the Periodic Table, held on a carrier.

The invention (II) is a catalyst for production of acetic acid, which is a catalyst used in a process for production of acetic acid by reaction of ethanol and oxygen that comprises (a) metallic palladium and (c) at least one element selected from the group consisting of Group 6 elements, Group 7 elements, Group 8 elements, Group 9 elements, Group 10 elements, Group 11 elements and Group 12 elements of the Periodic Table, held on a carrier.

The invention (III) is a catalyst for production of acetic acid, which is a catalyst used in a process for production of acetic acid by reaction of ethanol and oxygen that comprises (a) metallic palladium, (b) at least one element selected from the group consisting of Group 14 elements, Group 15 elements and Group 16 elements of the Periodic Table and (c) at least one element selected from the group consisting of Group 6 elements, Group 7 elements, Group 8 elements, Group 9 elements, Group 10 elements, Group 11 elements and Group 12 elements of the Periodic Table, held on a carrier.

The invention (IV) is a process for production of a catalyst according to any one of the inventions (I) to (III).

The invention (V) is a process for production of acetic acid from ethanol and oxygen using a catalyst according to any one of the inventions (I) to (III).

The invention (VI) is a catalyst for production of acetic acid and ethyl acetate, which is a catalyst used in a process for production of acetic acid and ethyl acetate by reaction of ethanol and oxygen that comprises (a) metallic palladium and (b) at least one compound selected-from the group consisting of inorganic acids and salts thereof.

The invention (VII) is a catalyst for production of acetic acid and ethyl acetate, which is a catalyst used in a process for production of acetic acid and ethyl acetate by reaction of ethanol and oxygen that comprises (a) metallic palladium, (b) at least one compound selected from the group consisting of inorganic acids and salts thereof, and (c) at least one element selected from the group consisting of Group 14 elements, Group 15 elements and Group 16 elements of the Periodic Table.

The invention (VIII) is a catalyst for production of acetic acid and ethyl acetate, which is a catalyst used in a process for production of acetic acid and ethyl acetate by reaction of ethanol and oxygen that comprises (a) metallic palladium, (b) at least one compound selected from the group consisting of inorganic acids and salts thereof, and (d) at least one element selected from the group consisting of Group 6 elements, Group 7 elements, Group 8 elements, Group 9 elements, Group 10 elements, Group 11 elements and Group 12 elements of the Periodic Table.

The invention (IX) is a catalyst for production of acetic acid and ethyl acetate, which is a catalyst used in a process for production of acetic acid and ethyl acetate by reaction of ethanol and oxygen that comprises (a) metallic palladium, (b) at least one compound selected from the group consisting of inorganic acids and salts thereof, (c) at least one element selected from the group consisting of Group 14 elements, Group 15 elements and Group 16 elements of the Periodic Table, and (d) at least one element selected from the group consisting of Group 6 elements, Group 7 elements, Group 8 elements, Group 9 elements, Group 10 elements, Group 11 elements and Group 12 elements of the Periodic Table.

The invention (X) is a catalyst for production of acetic acid and ethyl acetate according to any one of the inventions (VI) to (IX), wherein the catalyst components are held on a carrier.

The invention (XI) is a process for production of a catalyst according to any one of the inventions (VI) to (IX) that is not held on a carrier.

The invention (XII) is a process for production of the carrier-held catalyst of the invention (X).

The invention (XIII) is a process for production of acetic acid and ethyl acetate from ethanol and oxygen, using a catalyst according to any one of the inventions (VI) to (X).

BEST MODE FOR CARRYING OUT THE INVENTION

A catalyst for production of acetic acid according to the invention (I) will be explained first. The catalyst of the invention (I) is a catalyst for production of acetic acid which is a catalyst used in a process for production of acetic acid by reaction of ethanol and oxygen that comprises (a) metallic palladium and (b) at least one element selected from the group consisting of Group 14 elements, Group 15 elements and Group 16 elements of the Periodic Table (hereinafter may be referred to as group (b) element), held on a carrier.

The palladium contained in the catalyst of the invention (I) is metallic palladium, and it has a valency of 0. The metallic palladium can be obtained by using a reducing agent such as hydrazine, hydrogen or the like to reduce a divalent and/or tetravalent palladium ion. All of the palladium need not be in a metallic state.

As the (b) Group 14 elements, Group 15 elements and Group 16 elements of the Periodic Table used for the invention (I) there may be mentioned selenium, tellurium, antimony, tin, bismuth and lead, but there is no restriction to these. Tellurium, selenium, bismuth and antimony are particularly preferred for the group (b) elements in terms of catalyst performance and practicality.

The carrier used for the catalyst of the invention (I) is not particularly restricted, and it may be a common porous substance commonly used for carriers. As preferred substances there may be mentioned silica, alumina, silica-alumina, diatomaceous earth, montmorillonite and titania, or ion exchange resins, polymer-based carriers, etc. with silica being most preferred. The form of the carrier is not particularly restricted. Specifically there may be mentioned the forms of powder, spheres, pellets and the like, but there is no limitation to these. The particle size of the carrier is not especially restricted. The particle size of the carrier is preferably from about 1 mm to about 10 mm, and more preferably 3 to 8 mm. When the reaction is carried out by packing the catalyst into a cylindrical reactor, a particle size that is under 1 mm will result in a large pressure loss when the gas flows through, and this may result in problems such as an inability to achieve effective gas circulation. If the particle size is greater than 10 mm, the reaction gas can no longer diffuse into the catalyst interior, and this may impede effective catalytic reaction.

The pore volume of the carrier is not particularly restricted. It is preferably a pore volume of from about 0.2 ml to about 2.0 ml, and more preferably 0.3 to 1.5 ml, per gram of the carrier. There are no particular restrictions on the specific surface area of the carrier. It is preferably a specific surface area of 20 to 800 $m^2$, and more preferably 50 to 500 $m^2$, per gram of the carrier. There are also no particular restrictions on the pore diameter of the carrier. It is preferably in the range of 1 to 2000 nm, and more preferably 3 to 800 nm.

The catalyst for production of acetic acid according to the invention (I) is a binary catalyst containing (a) metallic palladium and a group (b) element. Although the structure of the catalyst has not been fully elucidated, the palladium is metallic palladium and the group (b) element is in the form of a metal, a compound or an alloy with metallic palladium, and when these are combined they are believed to exist very close together. The (a) metallic palladium and the group (b) element therefore interact expressing very high activity and selectivity.

The compositional ratio of the (a) metallic palladium and the one or more group (b) elements is preferably (a) 1 gram:(b) 0.005 to 10 grams, and more preferably (a) 1 gram:(b) 0.01 to 5 grams.

The loading amount of the (a) metallic palladium with respect to the carrier will differ depending on the particle size and pore structure of the carrier, but it is normally preferred to be in the range of 0.05–10 wt % with respect to the carrier. Although the reaction will still proceed adequately even if the palladium loading amount is under 0.1 wt %, this presents the risk of lower productivity. Also, although the reaction will still proceed adequately even if the amount is over 10 wt %, the high price of palladium renders this undesirable in economic and practical terms. In practice, the range is more preferably 0.2–6 wt %. Here, "wt %" with respect to the carrier refers to the value of the weight of the metallic palladium divided by the weight of the carrier.

The loading amount of the group (b) element with respect to the carrier will differ depending on the particle size and pore structure of the carrier, but it is preferably in the range of 0.0001–3 wt %, and more preferably in the range of 0.001–2.0 wt %, with respect to the carrier. Here, "wt %" with respect to the carrier refers to the value of the weight of the group (b) element divided by the weight of the carrier.

The amount of the components-in the catalyst according to the invention (I) can be measured in the following manner. After pulverizing a prescribed amount of the catalyst with a mortar or the like into a uniform powder, it is added to an acid such as hydrofluoric acid or aqua regia and dissolved by heating and stirring to prepare a homogeneous solution. The solution is then quantitatively analyzed with a plasma emission analyzer apparatus (for example, an SPS-1700 manufactured by Seiko Electronic Industries, KK.). The precision of the apparatus can be easily adjusted with commercially available standard reagents of different elements, and repeatable quantitation is possible.

A catalyst for production of acetic acid according to the invention (II) will now be explained. The catalyst of the invention (II) is a catalyst for production of acetic acid which is a catalyst used in a process for production of acetic acid by reaction of ethanol and oxygen that comprises (a) metallic palladium and (c) at least one element selected from the group consisting of Group 6 elements, Group 7 elements, Group 8 elements, Group 9 elements, Group 10 elements, Group 11 elements and Group 12 elements of the Periodic Table (hereinafter may be referred to as group (c) element), held on a carrier.

The (a) metallic palladium in the catalyst of the invention (II) is the same as for the catalyst of the invention (I). The carrier is also the same as for the catalyst of the invention (I).

The (c) Group 6 elements, Group 7 elements, Group 8 elements, Group 9 elements, Group 10 elements, Group 11 elements and Group 12 elements of the Periodic Table used in the catalyst of the invention (II) include, specifically, chromium, zinc, gold, nickel, ruthenium and the like, but there is no restriction to these. As preferred group (c) elements from the standpoint of catalyst performance and practicality there may be mentioned zinc, gold and chromium.

The catalyst for production of acetic acid according to the invention (II) is a binary catalyst containing (a) metallic palladium and a group (c) element. Although the structure of the catalyst has not been fully elucidated, the palladium is metallic palladium and the group (c) element is in the form of a metal, a compound or an alloy with metallic palladium, and when these are combined they are believed to exist very close together. The (a) metallic palladium and the group (c) element therefore interact expressing very high activity and selectivity, and exhibiting very low carbon dioxide selectivity with excellent acetic acid production activity and selectivity, compared to prior art catalysts.

The compositional ratio of the (a) metallic palladium and the one or more group (c) elements in the catalyst of the invention (II) is preferably (a) 1 gram:(c) 0.005 to 10 grams, and more preferably (a) 1 gram:(c) 0.01 to 5 grams.

The loading amount of the (a) metallic palladium with respect to the carrier is the same as for the catalyst of the invention (I).

The loading amount of the group (c) element with respect to the carrier will differ depending on the particle size and pore structure of the carrier, but it is preferably in the range of 0.0001–3 wt %, and more preferably in the range of 0.001–2 wt %, with respect to the carrier. Here, "wt %" with respect to the carrier refers to the value of the weight of the group (c) element divided by the weight of the carrier.

The amount of the components in the catalyst according to the invention (II) can be measured by the same method as for the catalyst of the invention (I).

A catalyst for production of acetic acid according to the invention (III) will now be explained. The catalyst of the invention (III) is a catalyst for production of acetic acid which is a catalyst used in a process for production of acetic acid by reaction of ethanol and oxygen that comprises (a) metallic palladium, (b) at least one element selected from the group consisting of Group 14 elements, Group 15 elements and Group 16 elements of the Periodic Table and (c) at least one element selected from the group consisting of Group 6 elements, Group 7 elements, Group 8 elements, Group 9 elements, Group 10 elements, Group 11 elements and Group 12 elements of the Periodic Table, held on a carrier.

The (a) metallic palladium in the catalyst of the invention (III) is the same as for the catalyst of the invention (I).

Also, in the catalyst of the invention (III), the (b) Group 14 elements, Group 15 elements and Group 16 elements of the Periodic Table are the same as for the catalyst of the invention (I), and the (c) Group 6 elements, Group 7 elements, Group 8 elements, Group 9 elements, Group 10 elements, Group 11 elements and Group 12 elements of the Periodic Table are the same as for the catalyst of the invention (II). The carrier is also the same as for the catalyst of the invention (II).

The catalyst for production of acetic acid according to the invention (III) is a ternary catalyst containing (a) metallic palladium, a group (b) element and a group (c) element. Although the structure of the catalyst has not been fully elucidated, the palladium is metallic palladium, and the group (b) element and the group (c) element are each in the form of a metal, a compound or an alloy with metallic palladium, and when these are combined they are believed to exist very close together. The (a) metallic palladium, the group (b) element and the group (c) element therefore interact expressing very high activity and selectivity, and exhibiting very low carbon dioxide selectivity with excellent acetic acid production activity and selectivity, compared to prior art catalysts.

The compositional ratio of the (a) metallic palladium, the one or more group (b) elements and the one or more group (c) elements in the catalyst of the invention (III) is preferably (a) 1 gram:(b) 0.005–10 grams:(c) 0.005 to 10 grams, and more preferably (a) 1 gram:(b) 0.01–5.0 grams:(c) 0.01 to 5 grams.

The loading amount of the (a) metallic palladium and the loading amount of the group (b) element with respect to the carrier are the same as for the catalyst of the invention (I), and the loading amount of the group (c) element is the same as for the catalyst of the invention (II).

The amount of the components in the catalyst according to the invention (III) can be measured by the same method as for the catalyst of the invention (I).

The process of the invention (IV) will now be explained. The process of the invention (IV) is a process for production of a catalyst for production of acetic acid according to the invention (I), (II) or (III).

The catalyst for production of acetic acid according to the invention (I) can be produced by the following production process (1) or (2).

Production process (1) for a catalyst for production of acetic acid according to the invention (I) comprises the following steps 1 and 2.

Step 1

A step wherein the (a) metallic palladium is loaded on a carrier to obtain a metallic palladium-loaded catalyst.

Step 2

A step wherein (b) at least one element selected from the group consisting of Group 14 elements, Group 15 elements and Group 16 elements of the Periodic Table is loaded on the metallic palladium-loaded catalyst obtained in step 1 to obtain a catalyst for production of acetic acid.

Production process (2) for a catalyst for production of acetic acid according to the invention (I) comprises the following steps 1 and 2.

Step 1

A step wherein a palladium compound and (b) at least one element selected from the group consisting of Group 14 elements, Group 15 elements and Group 16 elements of the Periodic Table are loaded on a carrier to obtain a palladium compound-loaded catalyst.

Step 2

A step wherein the palladium compound-loaded catalyst obtained in step 1 is reduced to obtain a catalyst for production of acetic acid.

In step 1 of production process (1) for a catalyst for production of acetic acid according to the invention (I), the palladium compound serving as the starting material for the metallic palladium is not particularly restricted. In most cases it is possible to use compounds that can be converted to palladium metal, for example, halides such as palladium chloride, organic acid salts such as palladium acetate, and also palladium nitrate, palladium oxide, palladium sulfate and sodium tetrachloropalladate, as well as palladium metal itself.

There are no particular restrictions on the method of loading the metallic palladium or the palladium compound that can be converted to metallic palladium on the carrier, and it may be loaded by any method. For example, when loading a palladium compound that can be converted to metallic palladium, the palladium compound may be dissolved or suspended in an appropriate solvent such as water or acetone, in an inorganic acid or organic acid such as hydrochloric acid, nitric acid, acetic acid, or the like, or a solution thereof, and then loaded onto the carrier and dried, as the method of loading onto the carrier.

As loading means there may be mentioned the impregnation method, evaporation to dry hardness method, kneading method and spray method, but there is no limitation to these.

When loading a palladium compound that can be converted to metallic palladium, there are no particular restrictions on the method of subsequently converting the palladium compound to metallic palladium, i.e. the method of reduction treatment. The reduction treatment may be carried out in either a liquid phase or vapor phase state, with no particular restrictions so long as the conditions are common reducing conditions.

Liquid phase reduction treatment is usually carried out at room temperature, but it may also be conducted with heating to a higher temperature of, specifically, about 30–50° C. Vapor phase reduction treatment is preferably carried out with heating of the palladium compound-loaded carrier to about 100–600° C. in order to achieve total conversion to palladium metal.

Specifically there may be mentioned a method whereby the palladium compound is reduced to metallic palladium by hydrazine, formalin, hydrogen, methanol, ethylene or the like, either directly or after treatment with an aqueous solution of sodium hydroxide, potassium hydroxide, barium hydroxide, sodium metasilicate, etc. to convert the palladium compound to an oxide, hydroxide, or the like.

The procedure for conversion of the palladium compound that can be converted to metallic palladium into metallic palladium may be carried out after separating the catalyst carrying the palladium compound, or it may be carried out immediately following the loading procedure. If conditions permit, it is preferably carried out immediately following the loading procedure, without separation. If necessary, the metallic palladium-loaded catalyst may be filtered by a common method and then washed and dried to remove any reaction-inhibiting substances for the catalytic reaction, such as halides or alkali salts of sodium, etc.

The metallic palladium-loaded catalyst can be obtained in the manner described above.

Step 2 of production process (1) for a catalyst for production of acetic acid according to the invention (I) is a step wherein (b) at least one element selected from the group consisting of Group 14 elements, Group 15 elements and Group 16 elements of the Periodic Table is loaded on the metallic palladium-loaded catalyst obtained in step 1 to obtain a catalyst for production of acetic acid.

The starting material of the (b) at least one element selected from the group consisting of Group 14 elements, Group 15 elements and Group 16 elements of the Periodic Table is not particularly restricted, and it may be the element itself or a halide, nitrate, acetate, phosphate, sulfate or oxide containing the element, or even a complex with an organic molecule such as acetylacetonato or nitrile as the ligand.

Specifically there may be mentioned chlorides such as selenium chloride, tellurium chloride, antimony chloride, tin chloride, bismuth chloride, lead chloride, etc.; nitrates such as antimony nitrate, tin nitrate, bismuth nitrate, lead nitrate, etc.; acetates such as tin acetate, bismuth acetate, lead acetate, etc.; and selenium oxide, selenic acid ($H_2SeO_4$) and its salts, selenious acid ($H_2SeO_3$) and its salts, metallic selenium, tellurium oxide, telluric acid ($H_6TeO_6$) and its salts, tellurous acid ($H_2TeO_3$) and its salts, metallic tellurium and the like, but there is no limitation to these.

There are no particular restrictions on the method of loading the starting material for the group (b) element on the carrier, and it may be loaded by any method. For example, the starting material for the group (b) element may be dissolved or suspended in an appropriate solvent such as water or acetone, or in an inorganic acid or organic acid such as hydrochloric acid, nitric acid, acetic acid, or the like and then impregnated into the carrier and dried, as the method of loading onto the carrier.

As loading means there may be mentioned the impregnation method, evaporation to dry hardness method, kneading method and spray method, but there is no limitation to these.

A catalyst for production of acetic acid according to the invention (I) can be obtained in the manner described above.

Step 1 of production process (2) for a catalyst for production of acetic acid according to the invention (I) is a step wherein a palladium compound and (b) at least one element selected from the group consisting of Group 14 elements, Group 15 elements and Group 16 elements of the Periodic Table are loaded on a carrier to obtain a palladium compound-loaded catalyst.

In step 1 of production process (2) for a catalyst for production of acetic acid according to the invention (I), the palladium compound serving as the starting material for the metallic palladium and its loading method are the same as in step 1 of production process (1) for a catalyst for production of acetic acid according to the invention (I).

The starting material for the group (b) element and its loading method are also the same as in step 2 of production process (1) for a catalyst for production of acetic acid according to the invention (I).

The loading of the palladium compound that can be converted to metallic palladium on the carrier and the loading of the starting material for the group (b) element on the carrier may be carried out in any order. That is, both loadings may be carried out simultaneously, or one before the other. However, it is preferred for loading of the group (b) element on the carrier to be carried out simultaneously with loading of the palladium compound.

The palladium compound-loaded catalyst can be obtained in the manner described above.

Step 2 of production process (2) for a catalyst for production of acetic acid according to the invention (I) is a step wherein the palladium compound-loaded catalyst obtained in step 1 is reduced to obtain a catalyst for production of acetic acid.

For a catalyst having a palladium compound that can be converted to metallic palladium and/or a starting compound for a group (b) element held on a carrier, the method for conversion of these compounds to their respective metal elements, i.e. the method of reduction treatment, is not particularly restricted. The reduction treatment is the same as in step 1 of production process (1) for a catalyst for production of acetic acid according to the invention (I).

A catalyst for production of acetic acid according to the invention (I) can be obtained in the manner described above.

A catalyst for production of acetic acid according to the invention (II) can be produced by the following production process (3) or (4).

Production process (3) for a catalyst for production of acetic acid according to the invention (II) comprises the following steps 1 and 2.

Step 1

A step wherein the (a) metallic palladium is loaded on a carrier to obtain a metallic palladium-loaded catalyst.

Step 2

A step wherein (c) at least one element selected from the group consisting of Group 6 elements, Group 7 elements, Group 8 elements, Group 9 elements, Group 10 elements, Group 11 elements and Group 12 elements of the Periodic Table is loaded on the metallic palladium-loaded catalyst obtained in step 1 to obtain a catalyst for production of acetic acid.

Production process (4) for a catalyst for production of acetic acid according to the invention (II) comprises the following steps 1 and 2.

Step 1

A step wherein a palladium compound and (c) at least one element selected from the group consisting of Group 6 elements, Group 7 elements, Group 8 elements, Group 9 elements, Group 10 elements, Group 11 elements and Group 12 elements of the Periodic Table are loaded on a carrier to obtain a palladium compound-loaded catalyst.

Step 2

A step wherein the palladium compound-loaded catalyst obtained in step 1 is reduced to obtain a catalyst for production of acetic acid.

In step 1 of production process (3) for a catalyst for production of acetic acid according to the invention (II), the palladium compound serving as the starting material for the metallic palladium, its loading method and the method for its conversion to metallic palladium are the same as in step 1 of production process (1) for a catalyst for production of acetic acid according to the invention (I).

Step 2 in production process (3) for a catalyst for production of acetic acid according to the invention (II) is step wherein (c) at least one element selected from the group consisting of Group 6 elements, Group 7 elements, Group 8 elements, Group 9 elements, Group 10 elements, Group 11 elements and Group 12 elements of the Periodic Table is loaded on the metallic palladium-loaded catalyst obtained in step 1 to obtain a catalyst for production of acetic acid.

The (c) at least one element selected from the group consisting of Group 6 elements, Group 7 elements, Group 8 elements, Group 9 elements, Group 10 elements, Group 11 elements and Group 12 elements of the Periodic Table is not particularly restricted, and it may be the element itself or a halide, nitrate, acetate, phosphate, sulfate or oxide containing the element, or even a complex with an organic molecule such as acetylacetonato or nitrile as the ligand.

Specifically there may be mentioned chlorides such as chromium chloride, manganese chloride, rhenium chloride, ruthenium chloride, rhodium chloride, iridium chloride, nickel chloride, tetrachloro aurate and its salts, chlorides such as zinc chloride, etc.; nitrates such as chromium nitrate, manganese nitrate, nickel nitrate, iridium nitrate, zinc nitrate, etc.; acetates such as chromium acetate, manganese acetate, rhenium acetate, ruthenium acetate, iridium acetate, nickel acetate, zinc acetate, and the like, but there is no limitation to these.

There are no particular restrictions on the method of loading the starting material for the group (c) element on the carrier, and it may be loaded by any method. For example, the starting material for the group (c) element may be dissolved or suspended in an appropriate solvent such as water or acetone, or in an inorganic acid or organic acid such as hydrochloric acid, nitric acid, acetic acid or the like and then impregnated into the carrier and dried, as the method of loading onto the carrier. As loading means there may be mentioned the impregnation method, evaporation to dry hardness method, kneading method and spray method, but there is no limitation to these.

A catalyst for production of acetic acid according to the invention (II) can be obtained in the manner described above.

Step 1 in production process (4) for a catalyst for production of acetic acid according to the invention (II) is a step wherein a palladium compound and (c) at least one element selected from the group consisting of Group 6 elements, Group 7 elements, Group 8 elements, Group 9 elements, Group 10 elements, Group 11 elements and Group 12 elements of the Periodic Table are loaded on a carrier to obtain a palladium compound-loaded catalyst.

In production process (4) for a catalyst for production of acetic acid according to the invention (II), the palladium compound serving as the starting material for the metallic palladium and its loading method are the same as in step 1 of production process (1) for a catalyst for production of acetic acid according to the invention (I).

The starting material for the group (c) element and its loading method are the same as in step 2 of production process (i) for a catalyst for production of acetic acid according to the invention (II).

The loading of the palladium compound that can be converted to metallic palladium on the carrier and the loading of the starting material for the group (c) element on the carrier may be carried out in any order. That is, both loadings may be carried out simultaneously, or one before the other. However, it is preferred for loading of the group (c) element on the carrier to be carried out simultaneously with loading of the palladium compound.

Step 2 in production process (4) for a catalyst for production of acetic acid according to the invention (II) is step wherein the palladium compound-loaded catalyst obtained in step 1 is reduced to obtain a catalyst for production of acetic acid.

For a catalyst having a palladium compound that can be converted to metallic palladium and/or a starting compound for a group (c) element held on a carrier, the method for conversion of these compounds to their respective metal elements, i.e. the method of reduction treatment, is not particularly restricted. The reduction treatment is the same as in step 1 of production process (1) for a catalyst for production of acetic acid according to the invention (I).

A catalyst for production of acetic acid according to the invention (II) can be obtained in the manner described above.

A catalyst for production of acetic acid according to the invention (III) can be produced by the following production process (5) to (8).

Production process (5) for a catalyst for production of acetic acid according to the invention (III) comprises the following steps 1 and 2.

Step 1

A step wherein metallic palladium is loaded on a carrier to obtain a metallic palladium-loaded catalyst.

Step 2

A step wherein (b) at least one element selected from the group consisting of Group 14 elements, Group 15 elements and Group 16 elements of the Periodic Table and (c) at least one element selected from the group consisting of Group 6 elements, Group 7 elements, Group 8 elements, Group 9 elements, Group 10 elements, Group 11 elements and Group 12 elements of the Periodic Table are loaded on the metallic palladium-loaded catalyst obtained in step 1 to obtain a catalyst for production of acetic acid.

Production process (6) for a catalyst for production of acetic acid according to the invention (III) comprises the following steps 1 and 2.

Step 1

A step wherein a palladium compound, (b) at least one element selected from the group consisting of Group 14 elements, Group 15 elements and Group 16 elements of the Periodic Table and (c) at least one element selected from the group consisting of Group 6 elements, Group 7 elements, Group 8 elements, Group 9 elements, Group 10 elements, Group 11 elements and Group 12 elements of the Periodic Table are loaded on a carrier to obtain a palladium compound-loaded catalyst.

Step 2

A step wherein the palladium compound-loaded catalyst obtained in step 1 is reduced to obtain a catalyst for production of acetic acid.

Production process (7) for a catalyst for production of acetic acid according to the invention (III) comprises the following steps 1 to 3.

Step 1

A step wherein a palladium compound and (b) at least one element selected from the group consisting of Group 14 elements, Group 15 elements and Group 16 elements of the Periodic Table are loaded on a carrier to obtain a palladium compound-loaded catalyst.

Step 2

A step wherein the palladium compound-loaded catalyst obtained in step 1 is reduced to obtain a metallic palladium-loaded catalyst.

Step 3

A step wherein (c) at least one element selected from the group consisting of Group 6 elements, Group 7 elements, Group 8 elements, Group 9 elements, Group 10 elements, Group 11 elements and Group 12 elements of the Periodic Table is loaded on the metallic palladium-loaded catalyst obtained in step 2 to obtain a catalyst for production of acetic acid.

Production process (8) for a catalyst for production of acetic acid according to the invention (III) comprises the following steps 1 to 3.

Step 1

A step wherein a palladium compound and (c) at least one element selected from the group consisting of Group 6 elements, Group 7 elements, Group 8 elements, Group 9 elements, Group 10 elements, Group 11 elements and Group 12 elements of the Periodic Table are loaded on a carrier to obtain a palladium compound-loaded catalyst.

Step 2

A step wherein the palladium compound-loaded catalyst obtained in step 1 is reduced to obtain a metallic palladium-loaded catalyst.

Step 3

A step wherein (b) at least one element selected from the group consisting of Group 14 elements, Group 15 elements and Group 16 elements of the Periodic Table is loaded on the metallic palladium-loaded catalyst obtained in step 2 to obtain a catalyst for production of acetic acid.

In step 1 of production process (5) for a catalyst for production of acetic acid according to the invention (III), the palladium compound serving as the starting material for the metallic palladium, its loading method and the method for its conversion to metallic palladium are the same as in step 1 of production process (1) for a catalyst for production of acetic acid according to the invention (I).

In step 2 of production process (5) for a catalyst for production of acetic acid according to the invention (III), the starting material for the (b) at least one element selected from the group consisting of Group 14 elements, Group 15 elements and Group 16 elements of the Periodic Table and its loading method are the same as in step 2 of production process (1) for a catalyst for production of acetic acid according to the invention (I).

The starting material for the group (c) element and its loading method are the same as in step 2 of production process (3) for a catalyst for production of acetic acid according to the invention (II).

A catalyst for production of acetic acid according to the invention (III) can be obtained in the manner described above.

In step 1 of production process (6) for a catalyst for production of acetic acid according to the invention (III), the palladium compound serving as the starting material for the metallic palladium and its loading method are the same as in step 1 of production process (1) for a catalyst for production of acetic acid according to the invention (I).

The starting material for the group (b) element and its loading method are the same as in step 2 of production process (1) for a catalyst for production of acetic acid according to the invention (I).

The starting material for the group (c) element and its loading method are the same as in step 2 of production process (3) for a catalyst for production of acetic acid according to the invention (II).

The loading of the palladium compound that can be converted to metallic palladium on the carrier, the loading of the starting material for the group (b) element on the carrier and the loading of the starting material for the group (c) element on the carrier may be carried out in any order. That is, all of the loadings may be carried out simultaneously, or one before the others. However, it is preferred for loading of the group (c) element on the carrier to be carried out simultaneously with loading of the palladium compound.

The palladium compound-loaded catalyst can be obtained in the manner described above.

Step 2 of production process (6) for a catalyst for production of acetic acid according to the invention (III) is a step wherein the palladium compound-loaded catalyst obtained in step 1 is reduced to obtain a catalyst for production of acetic acid.

For a catalyst having a palladium compound that can be converted to metallic palladium, a starting compound for a group (b) element and a starting compound for a group (c) element held on a carrier, the method for conversion of these compounds to their respective metal elements, i.e. the method of reduction treatment, is not particularly restricted. The reduction treatment is the same as in step 1 of production process (1) for a catalyst for production of acetic acid according to the invention (I).

In step 1 of production process (7) for a catalyst for production of acetic acid according to the invention (III), the palladium compound serving as the starting material for the metallic palladium and its loading method are the same as in step 1 of production process (1) for a catalyst for production of acetic acid according to the invention (I).

The starting material for the group (b) element and its loading method are the same as in step 2 of production process (1) for a catalyst for production of acetic acid according to the invention (I).

The loading of the palladium compound that can be converted to metallic palladium on the carrier and the loading of the starting material for the group (b) element on the carrier may be carried out in any order. That is, both loadings may be carried out simultaneously, or one before the other. However, it is preferred for loading of the group (b) element on the carrier to be carried out simultaneously with loading of the palladium compound.

The palladium compound-loaded catalyst can be obtained in the manner described above.

Step 2 of production process (7) for a catalyst for production of acetic acid according to the invention (III) is a step wherein the palladium compound-loaded catalyst obtained in step 1 is reduced to obtain a metallic palladium-loaded catalyst.

For a catalyst having a palladium compound that can be converted to metallic palladium and a starting compound for a group (b) element held on a carrier, the method for conversion of these compounds to their respective metal elements, i.e. the method of reduction treatment, is not particularly restricted. The reduction treatment is the same as in step 1 of production process (1) for a catalyst for production of acetic acid according to the invention (I).

The metallic palladium-loaded catalyst can be obtained in the manner described above.

Step 3 of production process (7) for a catalyst for production of acetic acid according to the invention (III) is a step wherein a group (c) element is loaded on the metallic palladium-loaded catalyst obtained in step 2 to obtain a catalyst for production of acetic acid.

The starting material for the group (c) element and its loading method are the same as in step 2 of production process (3) for a catalyst for production of acetic acid according to the invention (II).

A catalyst for production of acetic acid according to the invention (III) can be obtained in the manner described above.

In step 1 of production process (8) for a catalyst for production of acetic acid according to the invention (III), the palladium compound serving as the starting material for the metallic palladium and its loading method are the same as in step 1 of production process (3) for a catalyst for production of acetic acid according to the invention (II).

The starting material for the group (c) element and its loading method are the same as in step 2 of production process (3) for a catalyst for production of acetic acid according to the invention (II).

The loading of the palladium compound that can be converted to metallic palladium on the carrier and the loading of the starting material for the group (c) element on the carrier may be carried out in any order. That is, both loadings may be carried out simultaneously, or one before the other. However, it is preferred for loading of the group (c) element on the carrier to be carried out simultaneously with loading of the palladium compound.

The palladium compound-loaded catalyst can be obtained in the manner described above.

Step 2 of production process (8) for a catalyst for production of acetic acid according to the invention (III) is a step wherein the palladium compound-loaded catalyst obtained in step 1 is reduced to obtain a metallic palladium-loaded catalyst.

For a catalyst having a palladium compound that can be converted to metallic palladium and a starting compound for a group (c) element held on a carrier, the method for conversion of these compounds to their respective metal elements, i.e. the method of reduction treatment, is not particularly restricted. The reduction treatment is the same as in step 1 of production process (1) for a catalyst for production of acetic acid according to the invention (I).

The metallic palladium-loaded catalyst can be obtained in the manner described above.

Step 3 of production process (8) for a catalyst for production of acetic acid according to the invention (III) is a step wherein a group (b) element is loaded on the metallic palladium-loaded catalyst obtained in step 2 to obtain a catalyst for production of acetic acid.

The starting material for the group (b) element and its loading method are the same as in step 2 of production process (1) for a catalyst for production of acetic acid according to the invention (I).

A catalyst for production of acetic acid according to the invention (III) can be obtained in the manner described above.

The invention (V) is a process for production of acetic acid from ethanol and oxygen using a catalyst for production-of acetic acid according to any one of the inventions (I), (II) or (III).

The reaction process is not particularly restricted so long as it allows a catalyst of the invention to react ethanol with oxygen, and it may be any of a variety of processes including a batch process, semi-batch process, semi-continuous process, continuous flow process or a combination thereof, for a vapor phase reaction or liquid phase reaction.

The ethanol starting material may be supplied in liquid form, or it may be supplied in vapor form. That is, the reaction process may be, for example, a semi-continuous process whereby the catalyst of the invention is suspended in liquid ethanol and/or an ethanol solution and oxygen is passed through, or a continuous flow process whereby ethanol and oxygen gas are passed through the catalyst. A vapor phase reaction process is preferred from the standpoint of separation of the catalyst, starting materials and products, and from the standpoint of acetic acid productivity. More preferred, and advantageous in practical terms, is to employ a fixed bed having corrosion-resistant reaction tubes packed with the catalyst of the invention, for a vapor phase reaction process in which the ethanol and oxygen are passed through.

A vapor phase reaction and liquid phase reaction used in the process for production of acetic acid according to the invention (V) will now be explained.

A vapor phase reaction will be explained first.

There are no particular restrictions on the reaction temperature for production of acetic acid by reaction of ethanol and oxygen in a vapor phase according to the acetic acid production method of the invention (V), but it is preferably 100–250° C. If the reaction temperature is below 100° C. the reaction rate may be insufficient, while if it is above 250° C. a greater number of secondary reactions will tend to occur. More preferred in practical terms is the range of 120–230° C.

The reaction pressure is not particularly restricted but in terms of the equipment it is advantageous in practice for it to be from 0.0 to 3.0 MPa (gauge pressure). It is more preferably in the range of 0.1 to 1.5 MPa (gauge pressure), In the case of a flow-type reaction, the gas supplied to the reaction system comprises ethanol and oxygen, and if necessary nitrogen, carbon dioxide, a rare gas or the like may also be used as a diluent. The ethanol is supplied to the reaction system in an amount corresponding to a proportion of 0.01–50% by volume, and especially 0.1–40% by volume, and the oxygen in an amount corresponding to a proportion of 1–15% by volume, and especially 2–10% by volume, with respect to the total amount of supply gas. Here, an ethanol concentration exceeding 20% by volume will tend to increase the degree of secondary reactions, while a concentration of under 2% by volume will tend to lower the productivity.

The presence of water in the reaction system will provide a notable effect of improved acetic acid production activity and selectivity, as well as prolonged activity of the catalyst in the reaction system. It is suitable for water vapor to be included in the reaction gas at 0.1–50% by volume. If the water vapor in the reaction gas is present at less than 0.1% by volume the catalyst may tend to undergo deterioration more readily, and if it is present at greater than 50% by volume, the steam unit requirement may be poorer. In practical terms, the range is most preferably 0.5–40% by volume.

When carrying out the production process for acetic acid of the invention according to this gas phase reaction there are no particular restrictions on the ethanol starting material. It is advantageous to use a high purity ethanol starting material, but there is no problem with mixing a small amount of a lower saturated hydrocarbon such as methane, ethane or propane or the like.

There are also no particular restrictions on the oxygen, and it may be in a form such as air, diluted with an inert gas such as nitrogen, carbon dioxide gas or the like. When the reaction gas is circulated it is generally more advantageous to use oxygen at a high concentration, preferably 99% or greater.

The reaction mixture gas consisting of ethanol and oxygen may be blended with acetaldehyde, diethyl ether or the like and supplied to the reaction system. Acetaldehyde and/or diethyl ether to be supplied together with the reaction mixture gas may be in an amount of the range of preferably 0.001–5.0% by volume, more preferably 0.01–4.0% by volume in the total reaction mixture gas.

The reaction mixture gas is preferably passed through the catalyst at a space velocity (SV) in the range of 500–15,000 $hr^{-1}$, and especially 1000–10,000 $hr^{-1}$, in a standard state.

Next, a liquid phase reaction will be explained.

There are no particular restrictions on the reaction temperature for production of acetic acid by reaction of ethanol and oxygen in a liquid phase according to the acetic acid production method of the invention (V), but it is preferably 0–200° C. If the reaction temperature is below 0° C. the reaction rate may be insufficient, while if it is above 200° C. a greater number of secondary reactions may occur. More preferred in practical terms is the range of 20–100° C.

The reaction pressure is not particularly restricted but in terms of the equipment it is advantageous in practice for it to be from 0.0 to 3.0 MPa (gauge pressure). It is more preferably in the range of 0.1 to 1.5 MPa (gauge pressure).

The ethanol and/or oxygen starting materials may be present in the catalyst beforehand, or they may be added at an appropriate point during the reaction. When they are supplied to the reaction system, they may be in gaseous and/or liquid form.

The starting material supplied to the reaction system comprises ethanol and oxygen, and if necessary nitrogen, carbon dioxide or a diluting gas may also be used.

The presence of water in the reaction system will provide a notable effect of improved acetic acid production activity and selectivity, as well as prolonged activity of the catalyst in the reaction system. The proportion of water and ethanol in the reaction system is not particularly restricted. The proportion of water and ethanol may even be changed during the reaction, or an appropriate amount of water may be added to keep a constant proportion. If necessary, a basic component such as sodium hydroxide may be added to increase the reaction rate.

When carrying out the production process for acetic acid of the invention according to this liquid phase reaction there are no particular restrictions on the ethanol starting material. It is advantageous to use a high purity ethanol starting material, but there is no problem with mixing a small amount of a lower saturated hydrocarbon such as methane, ethane or propane or the like.

There are also no particular restrictions on the oxygen, and it may be in a form such as air, or diluted with an inert gas such as nitrogen, carbon dioxide gas or the like. When the reaction gas is circulated it is generally more advantageous to use oxygen at a high concentration, preferably 99% or greater.

The reaction mixture gas or liquid consisting of ethanol and oxygen may be blended with acetaldehyde, diethyl ether or the like and supplied to the reaction system.

The obtained acetic acid may be separated and purified by common methods to the desired degree of purity, in the case of either a gas phase reaction or a liquid phase reaction. When unreacted starting materials and by-products of acetaldehyde and/or diethyl ether remain, those unreacted starting materials and by-products of acetaldehyde and/or diethyl ether can be recovered and recycled into the reaction system for use.

When necessary, the catalyst used may be regenerated at an appropriate point or separated for repeated use.

A catalyst for production of acetic acid and ethyl acetate according to the inventions (VI) and (X) will now be explained.

The invention (VI) is a non-carrier-held catalyst for production of acetic acid and ethyl acetate, which is a catalyst used in a process for production of acetic acid and ethyl acetate by reaction of ethanol and oxygen that comprises (a) metallic palladium and (b) at least one compound selected from the group consisting of inorganic acids and salts thereof (hereinafter may be referred to as group (b)

compound) or a carrier-held catalyst for production of acetic acid and ethyl acetate wherein these catalyst components are held on a carrier is one of the catalysts according to the invention (X).

The palladium contained in the catalyst of the invention (VI) is metallic palladium, and it has a valency of 0. The metallic palladium can be obtained by using a reducing agent such as hydrazine, hydrogen or the like to reduce a divalent and/or tetravalent palladium ion. All of the palladium need not be in a metallic state.

As the inorganic acid of the group (b) compound there may be mentioned phosphoric acid, sulfuric acid, hydrochloric acid, nitric acid, niobic acid, heteropoly acids and the like, but there is no limitation to these. It is preferably phosphoric acid or a heteropoly acid.

A heteropoly acid is an acid formed by condensation of two or more inorganic oxyacids comprising a coordinated element (poly atom) and a central element (hetero atom). As the hetero atom in the heteropoly acid there may be mentioned phosphorus, silicon, boron, aluminum, germanium, cerium, cobalt and chromium, and as the poly atom there may be mentioned molybdenum, tungsten, vanadium, niobium and tantalum, but there are no particular restrictions. As specific examples there may be mentioned tungstosilicic acid, tungstophosphoiic acid, molybdosilicic acid, molybdophosphoric acid, molybdotungstophosphoric acid, molybdotungatosilicic acid, vanadotungstophosphoric acid, vanadotungstosilicic acid, vanadomolybdosilicic acid, vanadomolybdophosphoric acid, tungstoboric acid, molybdoboric acid and molybdotungstoboric acid.

Particularly preferred among these are heteropoly acids wherein the hetero atom is phosphorus or silicon and the polyatom is at least one element selected from the group consisting of tungsten, molybdenum and vanadium.

As the inorganic acid salt of the group (b) compound there may be mentioned metal salts or onium salts wherein all or a portion of the hydrogen atoms of the inorganic acid are substituted.

The metal element substituting the hydrogen atoms of the inorganic acid is not particularly restricted. Specific examples are at least one element selected from the group consisting of Group 1, Group 2, Group 6, Group 7, Group 8, Group 9, Group 10, Group 11, Group 12 and Group 13 elements of the Periodic Table, and examples of onium salts of the inorganic acid include ammonium salts with ammonium or amines. Particularly preferred among these inorganic acid salts are metal salts of lithium, sodium, potassium, cesium, rubidium, chromium, barium, cobalt, nickel, manganese and copper.

While the structure of the catalyst has not been fully elucidated, the palladium is (a) metallic palladium, and the group (b) compound is a compound with definite acidity. The elements and compounds of these two groups (a) and (b) are believed to exist very close together, the compounds and elements of each group interacting to express very high activity and selectivity.

The compositional ratio of the (a) metallic palladium and the group (b) compound is preferably (a) 1 gram:(b) 0.025–500 grams and more preferably (a) 1 gram:(b) 0.1–400 grams.

There are no particular restrictions on the content of the (a) metallic palladium in the catalyst. However, it is preferably in the range of 0.001–10 wt %. Although the reaction will still proceed adequately even if the content of the (a) metallic palladium is under 0.001 wt %, this presents the risk of lower practical productivity. Also, although the reaction will still proceed adequately even if the content of the (a) metallic palladium is over 10 wt %, the high price of palladium renders this undesirable in economic and practical terms. In practice, the range is more preferably 0.005–8.0 wt %. Here, "wt %" refers to the proportion of the weight of the (a) metallic palladium in the catalyst with respect to the weight of the total catalyst.

The catalyst may be effectively used with only the catalyst substance having the aforementioned composition, or it may be loaded on a carrier for more advantageous use.

The carrier used is suitably porous silica, alumina, silica-alumina, diatomaceous earth, montmorillonite, titania, an ion exchange resin or a polymer-based carrier, with silica being most suitable. The carrier may be in the form of a powder, spheres, pellets or any other desired form.

The particle size of the carrier is preferably 1–10 mm. When the reaction is carried out by packing the catalyst into a cylindrical reactor, a particle size that is under 1 mm will result in a large pressure loss when the gas flows through, and this may make it impossible to achieve effective gas circulation. If the particle size is over 10 mm, the reaction gas can no longer diffuse into the catalyst interior, and this may impede effective catalytic reaction. The particle size is more preferably 3–8 mm.

The pore volume of the carrier is preferably a pore volume of 0.2–2.0 ml, and more preferably 0.3–1.5 ml, per gram of the carrier. The specific surface area of the carrier is preferably a specific surface area of 20–800 $m^2$, and more preferably 50–500 $m^2$, per gram of the carrier. The pore diameter of the carrier is preferably 1–2000 nm, and more preferably 3–800 nm.

The loading amount of the (a) metallic palladium with respect to the carrier will differ depending on the particle size and pore structure of the carrier, but it is normally preferred to be in the range of 0.01–10 wt % with respect to the carrier. Although the reaction will still proceed adequately even if the content of the palladium loading amount is under 0.01 wt %, this presents the risk of lower productivity. Also, although the reaction will still proceed adequately even if the amount is over 10 wt %, the high price of palladium renders this undesirable in economic and practical terms. In practice, the range is more preferably 0.2–6 wt %. Here, "wt %" refers to the proportion of the weight of the (a) metallic palladium in the catalyst with respect to the weight of the carrier.

The loading amount of the group (b) compound with respect to the carrier will also differ depending on the particle size and pore structure of the carrier, but it is preferably in the range of 5–200 wt %, and more preferably in the range of 10–100 wt %, with respect to the carrier. Here, "wt %" refers to the proportion of the weight of the group (b) compound in the catalyst with respect to the weight of the carrier.

The invention (VII) is a non-carrier-held catalyst for production of acetic acid and ethyl acetate, which is a catalyst used in a process for production of acetic acid and ethyl acetate by reaction of ethanol and oxygen that comprises (a) metallic palladium, (b) at least one compound selected from the group consisting of inorganic acids and salts thereof, and (c) at least one element selected from the group consisting of Group 14 elements, Group 15 elements and Group 16 elements of the Periodic Table (hereinafter may be referred to as group (c) element) or a carrier-held catalyst for production of acetic acid and ethyl acetate wherein these catalyst components are held on a carrier is one of the catalysts according to the invention (X).

The catalyst of the invention (VII) is the catalyst of the invention (VI) which contains a group (c) element, and it is a ternary catalyst.

The (a) metallic palladium and the group (b) compound used for the invention (VII) are the same as according to the invention (VI).

The (c) Group 14 elements, Group 15 elements and Group 16 elements of the Periodic Table include selenium, tellurium, antimony, tin, bismuth and lead. Selenium, tellurium, tin and bismuth are preferred.

Although the structure of the catalyst has not been fully elucidated, the (a) metallic palladium and the group (b) compound are the same as for the catalyst of the invention (VI), and the same effect may be expected as with the catalyst of the invention (VI). The elements and compounds of these three groups (a), (b) and (c) are believed to exist very close together. The (a) metallic palladium, the group (b) compound and the group (c) element therefore interact expressing very high activity and selectivity, i.e. exhibiting low selectivity for carbon dioxide and acetaldehyde while exhibiting excellent production activity and selectivity for acetic acid and ethyl acetate.

The compositional ratio of the (a) metallic palladium, the group (b) compound and the group (c) element in the catalyst is preferably (a) 1 gram:(b) 0.025–500 grams:(c) 0.005–10 grams, and more preferably (a) 1 gram:(b) 0.1–400 grams:(c) 0.01–5 grams. The content of the (a) metallic palladium in this catalyst is the same as for the catalyst of the invention (VI).

For loading on a carrier, the carrier is also the same as for the catalyst of the invention (VI).

The loading amounts of the (a) metallic palladium and the group (b) compound with respect to the carrier are the same as for the catalyst of the invention (VI).

The loading amount of the group (c) element with respect to the carrier will differ depending on the particle size and pore structure of the carrier, but it is preferably in the range of 0.0001–3.0 wt %, and more preferably in the range of 0.001–2.0 wt %, with respect to the carrier. Here, "wt %" refers to the proportion of the weight of the group (c) element in the catalyst with respect to the weight of the carrier.

The invention (VIII) is a non-carrier-held catalyst for production of acetic acid and ethyl acetate, which is a catalyst used in a process for production of acetic acid and ethyl acetate by reaction of ethanol and oxygen that comprises (a) metallic palladium, (b) at least one compound selected from the group consisting of inorganic acids and salts thereof, and (d) at least one element selected from the group consisting of Group 6 elements, Group 7 elements, Group 8 elements, Group 9 elements, Group 10 elements, Group 11 elements and Group 12 elements of the Periodic Table (hereinafter may be referred to as group (d) element) or a carrier-held catalyst for production of acetic acid and ethyl acetate wherein these catalyst components are held on a carrier is one of the catalysts according to the invention (X).

The catalyst of the invention (VIII) is the catalyst of the invention (VI) which contains a group (d) element, and it is a ternary catalyst.

The (a) metallic palladium and the group (b) compound used for the invention (VIII) are the same as according to the invention (VI).

As the (d) Group 6 elements, Group 7 elements, Group 8 elements, Group 9 elements, Group 10 elements, Group 11 elements and Group 12 elements of the Periodic Table there may be mentioned chromium, manganese, rhenium, ruthenium, rhodium, iridium, nickel, gold and zinc. Chromium, manganese, gold and zinc are preferred.

Although the structure of the catalyst has not been fully elucidated, the (a) metallic palladium and the group (b) compound are the same as for the catalyst of the invention (VI), and the same effect may be expected as with the catalyst of the invention (VI). The elements and compounds of these three groups (a), (b) and (d) are believed to exist very close together. The (a) metallic palladium, the group (b) compound and the group (d) element therefore interact expressing very high activity and selectivity, i.e. exhibiting low selectivity for carbon dioxide and acetaldehyde while exhibiting excellent production activity and selectivity for acetic acid and ethyl acetate.

The compositional ratio of the (a) metallic palladium, the group (b) compound and the group (d) element in the catalyst is preferably (a) 1 gram:(b) 0.025–500 grams:(d) 0.005–10 grams, and more preferably (a) 1 gram:(b) 0.1–400 grams:(d) 0.01–5 grams. The content of the (a) metallic palladium in this catalyst is the same as for the invention (VI).

For loading on a carrier, the carrier is also the same as for the catalyst of the invention (VI).

The loading amounts of the (a) metallic palladium and the group (b) compound with respect to the carrier are the same as for the catalyst of the invention (VI).

The loading amount of the group (d) element with respect to the carrier will differ depending on the particle size and pore structure of the carrier, but it is preferably in the range of 0.0001–3.0 wt %, and more preferably in the range of 0.001–2.0 wt %, with respect to the carrier. Here, "wt %" refers to the proportion of the weight of the group (d) element in the catalyst, with respect to the weight of the carrier.

The invention (IX) is a non-carrier-held catalyst for production of acetic acid and ethyl acetate, which is a catalyst used in a process for production of acetic acid and ethyl acetate by reaction of ethanol and oxygen that comprises (a) metallic palladium, (b) at least one compound selected from the group consisting of inorganic acids and salts thereof, (c) at least one element selected from the group consisting of Group 14 elements, Group 15 elements and Group 16 elements of the Periodic Table, and (d) at least one element selected from the group consisting of Group 6 elements, Group 7 elements, Group 8 elements, Group 9 elements, Group 10 elements, Group 11 elements and Group 12 elements of the Periodic Table on a carrier-held catalyst for production of acetic acid and ethyl acetate wherein these catalyst components are held on a carrier is one of the catalysts according to the invention (X).

The catalyst of the invention (IX) is the catalyst of the invention (VII) which contains a group (d) element, and it is a quaternary catalyst.

The (a) metallic palladium, the group (b) compound and the group (c) element used for the invention (IX) are the same as for the catalyst of the invention (VII). The (d) at least one element selected from the group consisting of Group 6 elements, Group 7 elements, Group 8 elements, Group 9 elements, Group 10 elements, Group 11 elements and Group 12 elements of the Periodic Table is the same as according to the invention (VIII).

Although the structure of the catalyst has not been fully elucidated, the (a) metallic palladium, the group (b) compound and the group (c) element are the same as for the catalyst of the invention (VII), and the same effect may be expected as by the catalyst of the invention (VII). The elements and compounds of these four groups (a), (b), (c) and (d) are believed to exist very close together. The (a) metallic palladium, the group (b) compound, the group (c) element and the group (d) element therefore interact expressing very high activity and selectivity, i.e. exhibiting low selectivity for carbon dioxide and acetaldehyde while exhibiting excellent production activity and selectivity for acetic acid and ethyl acetate.

The compositional ratio of the (a) metallic palladium, the group (b) compound, the group (c) element and the group (d) element in the catalyst is preferably (a) 1 gram:(b) 0.025–500 grams:(c) 0.005–10 grams:(d) 0.005–10 grams, and more preferably (a) 1 gram:(b) 0.1–400 grams:(c) 0.01–5 grams:(d) 0.01–5 grams. The content of the (a) metallic palladium in this catalyst is the same as for the catalyst of the invention (VI).

For loading on a carrier, the carrier is also the same as for the catalyst of the invention (VII).

The loading amounts of the (a) metallic palladium, the group (b) compound and the group (c) element with respect to the carrier are the same as for the catalyst of the invention (VII).

The loading amount of the group (d) element with respect to the carrier will differ depending on the particle size and pore structure of the carrier, but it is preferably in the range of 0.0001–3.0 wt %, and more preferably in the range of 0.001–2.0 wt %, with respect to the carrier. Here, "wt %" refers to the proportion of the weight of the group (d) element in the catalyst, with respect to the weight of the carrier.

A process for production of a non-carrier-held catalyst of any one of the inventions (VI) to (IX) according to the invention (XI) will now be explained. The process of the invention (XI) is a process for production of a non-carrier-held catalyst for production of acetic acid and ethyl acetate according to any one of the inventions (VI), (VII), (VIII) or (IX).

Production process (1) according to the invention (XI) is a process for production of a catalyst according to the invention (VI) that comprises the following steps 1 and 2.
Step 1
A step wherein a palladium suspension is obtained.
Step 2
A step wherein (b) at least one compound selected from the group consisting of inorganic acids and salts thereof is dissolved or suspended in the palladium suspension obtained in step 1, and the solvent is then removed.

Step 1 of production process (1) according to the invention (XI) is a step wherein a palladium suspension is obtained.

In production process (1) according to the invention (XI), there are no particular restrictions on the palladium compound as the starting material for the metallic palladium. Normally there may be used compounds that can be converted to metallic palladium, including halides such as palladium chloride, organic acid salts such as palladium acetate, and also palladium nitrate, palladium oxide, palladium sulfate and sodium tetrachloropalladate, or metallic palladium itself.

The palladium suspension can be obtained by dissolving or suspending the metallic palladium starting compound in an appropriate solvent.

The solvent used here may be water or an inorganic or organic solvent such as acetone, ethanol or the like, and if necessary an inorganic or organic acid such as hydrochloric acid, nitric acid or acetic acid may be dissolved in the solvent that is used. The metallic palladium starting compound is preferably one that can be homogeneously dissolved or suspended by stirring, etc., but it is not particularly restricted. If necessary, the metallic palladium starting compound may also be subjected to reduction treatment for conversion to metallic palladium.

In the case of reduction treatment in step 1, i.e. conversion to metallic palladium of the metallic palladium starting compound that can be converted to metallic palladium, the method used therefor is not particularly restricted. Specifically there may be mentioned a method whereby the metallic palladium starting compound is reduced to metallic palladium with an appropriate reducing agent such as hydrazine, formalin, methanol, ethylene, hydrogen or the like. The reduction treatment may be carried out in either a liquid phase or vapor phase state. Liquid phase reduction treatment is usually carried out at room temperature, but it may also be conducted with heating to a higher temperature, for example, about 30–50° C. Vapor phase reduction treatment is preferably-carried out with heating to about 100–600° C. in order to achieve total conversion to metallic palladium.

The palladium suspension can be obtained in this manner.

Step 2 of production process (1) according to the invention (XI) is a step wherein (b) at least one compound selected from the group consisting of inorganic acids and salts thereof is dissolved or suspended in the palladium suspension obtained in step 1, and the solvent is then removed to obtain a catalyst for production of acetic acid and ethyl acetate.

The group (b) compound which is used for this step is the same as for the catalyst of the invention (VI).

The method of dissolving or suspending the inorganic acid or salt thereof may be any method that produces homogeneity by stirring, etc., and it is not particularly restricted. For example, if it will dissolve it may be dissolved directly in the palladium suspension, and if it does not dissolve, a method may be employed whereby the inorganic acid or salt thereof is suspended in an appropriate solvent and the palladium suspension is added thereto dropwise.

The method of removing the solvent is not particularly restricted and may be any well-known method such as heating, pressure reduction, etc. In the case of heating, the temperature is preferably a temperature that does not cause decomposition of the inorganic acid. Particularly in the case of a heteropoly acid, a temperature of higher than 350° C. can result in decomposition, and this may impair the activity and selectivity of the catalyst produced by the method.

In step 2 as well, the metallic palladium starting compound may be subjected to reduction treatment if necessary for conversion to metallic palladium.

In the case of reduction treatment in step 2, i.e. conversion to metallic palladium of the metallic palladium starting compound that can be converted to metallic palladium, the method used therefor is not particularly restricted. Specifically there may be mentioned a method whereby the metallic palladium starting compound is reduced to metallic palladium with an appropriate reducing agent such as hydrazine, formalin, methanol, ethylene, hydrogen or the like. The reduction treatment may be carried out in either a liquid phase or vapor phase state.

Liquid phase reduction treatment is usually carried out at room temperature, but it may also be conducted with heating to a higher temperature, for example, about 30–50° C. Vapor phase reduction treatment is preferably carried out with heating to about 100–600° C. in order to achieve total conversion to metallic palladium.

The procedure for conversion to metallic palladium of the metallic palladium starting compound that can be converted to metallic palladium may be carried out while the metallic palladium starting compound containing (b) at least one compound selected from the group consisting of inorganic acids and salts thereof is in a suspended solution state, or after separation.

The catalyst of the invention (VI) can be obtained in the manner described above.

Production process (2) according to the invention (XI) will now be explained. Production process (2) according to the invention (XI) is a process for production of a catalyst according to the invention (VII), and it comprises step 1 and step 2 of production process (1) according to the invention (XI), as well as step 3 in which (c) at least one element selected from the group consisting of Group 14 elements, Group 15 elements and Group 16 elements of the Periodic Table is added in either or both of these steps.

The starting compound for the (a) metallic palladium used in step 1 of this process, and the method for its dissolution or suspension, are the same as in step 1 of production process (1) for the catalyst of the invention (VI), according to the invention (XI).

The starting material that gives the group (c) element is not particularly restricted, and it may be the element itself or a halide, nitrate, acetate, phosphate, sulfate or oxide containing the element, or even a complex with an organic molecule such as acetyl-acetonato or nitrile as the ligand.

Specifically there may be mentioned chlorides such as selenium chloride, tellurium chloride, antimony chloride, tin chloride, bismuth chloride, lead chloride, etc.; nitrates such as antimony nitrate, tin nitrate, bismuth nitrate, lead nitrate, etc.; acetates such as tin acetate, bismuth acetate, lead acetate, etc.; and selenium oxide, selenic acid ($H_2SeO_4$) and its salts, selenious acid ($H_2SeO_3$) and its salts, tellurium oxide, telluric acid ($H_6TeO_6$) and its salts, tellurous acid ($H_2TeO_3$) and its salts, metallic tellurium, potassium antimonate and the like, but there is no limitation to these.

The method of dissolving or suspending the starting compound for the group (c) element, when a group (c) element is added in step 1, may be any method that produces homogeneity by stirring, etc. with the metallic palladium starting compound, and it is not particularly restricted. For example, if it will dissolve it may be dissolved directly together with the starting compound of the metallic palladium, and if it does not dissolve, a method may be employed whereby the starting compound for the group (c) element is suspended in an appropriate solvent and the resulting solution is added dropwise to a solution in which the metallic palladium starting compound has been dissolved or suspended.

The solvent used here may be water or an inorganic or organic solvent such as acetone, ethanol or the like, and, if necessary, an inorganic acid or organic acid such as hydrochloric acid, nitric acid or acetic acid may be dissolved in the solvent that is used. The starting compound for the group (c) element is preferably one that can be homogeneously dissolved or suspended by stirring, etc., but it is not particularly restricted.

When a metallic palladium starting compound that can be converted to metallic palladium is converted to metallic palladium in step 1, the method therefor, i.e. the reduction treatment method, is the same as in step 1 of production process (1) according to the invention (XI).

The palladium suspension may be obtained in the manner described above.

The group (b) compound used for step 2 is the same as for the catalyst of the invention (VI), and the method of dissolving or suspending the group (b) compound and the method of removing the solvent are the same as in step 2 of production process (1) according to the invention (XI).

When a group (c) element is added in step 2, the starting compound for the element and the method of dissolving or suspending the starting compound for the group (c) element may be the same as in step 1 of production process (2) according to the invention (XI).

There are no particular restrictions on the order of adding the group (b) compound and the group (c) element to the palladium suspension, and two or more may be added simultaneously or in any desired order. That is, a group (b) compound and a group (c) element may be added simultaneously, or a group (c) element may be added and separated prior to adding the group (b) compound.

When a metallic palladium starting compound that can be converted to metallic palladium is converted to metallic palladium in step 2, the method therefor, i.e. the reduction treatment method, is the same as in step 2 of production process (1) according to the invention (XI).

The catalyst of the invention (VII) can be obtained in the manner described above.

Production process (3) according to the invention (XI) will now be explained. Production process (3) according to the invention (XI) is a process for production of a catalyst according to the invention (VIII), and it comprises step 1 and step 2 of production process (1) according to the invention (XI), as well as step 3 in which (d) at least one element selected from the group consisting of Group 6 elements, Group 7 elements, Group 8 elements, Group 9 elements, Group 10 elements, Group 11 elements and Group 12 elements of the Periodic Table is added in either or both of these steps.

The starting compound for the (a) metallic palladium used in step 1 of this process, and the method for its dissolution or suspension, are the same as in step 1 of production process (1) according to the invention (XI).

The starting material that gives the group (d) element is not particularly restricted, and it may be the element itself or a halide, nitrate, acetate, phosphate, sulfate or oxide containing the element, or even a complex with an organic molecule such as acetylacetonato or nitrile as the ligand. Specifically there may be mentioned chlorides such as chromium chloride, manganese chloride, rhenium chloride, ruthenium chloride, rhodium chloride, iridium chloride, nickel chloride, tetrachloro aurate and its salts, zinc chloride and its-salts, etc.; nitrates such as chromium nitrate, manganese nitrate, nickel nitrate, iridium nitrate, zinc nitrate, etc.; acetates such as chromium acetate, manganese acetate, rhenium acetate, ruthenium acetate, iridium acetate, nickel acetate, zinc acetate, and the like, but there is no limitation to these.

The method of dissolving or suspending the starting compound for the group (d) element, when it is added in step 1, may be any method that produces homogeneity by stirring, etc. with the metallic palladium starting compound, and it is not particularly restricted. For example, if it will dissolve it may be dissolved directly together with the starting compound of the metallic palladium, and if it does not dissolve, a method may be employed whereby the starting compound for the group (d) element is suspended in an appropriate solvent and the resulting solution is added dropwise to a solution in which the metallic palladium starting compound has been dissolved or suspended.

The solvent used here may be water or an inorganic or organic solvent such as acetone, ethanol or the like, and, if necessary, an inorganic. acid or organic acid such as hydrochloric acid, nitric acid or acetic acid may be dissolved in the solvent that is used. The starting compound for the group (d) element is preferably one that can be homogeneously dissolved or suspended by stirring, etc., but it is not particularly restricted.

When a metallic palladium starting compound that can be converted to metallic palladium is converted to metallic palladium in step 1, the method therefor, i.e. the reduction treatment method, is the same as in step 1 of production process (1) according to the invention (XI).

The palladium suspension may be obtained in the manner described above.

The group (b) compound used for step 2 is the same as for the catalyst of the invention (VI), and the method of dissolving or suspending the group (b) compound and the method of removing the solvent are the same as in step 2 of production process (1) for the catalyst of the invention (VI), according to the invention (XI).

When a group (d) element is added in step 2, the starting compound for the element and the method of dissolving or suspending the starting compound for the group (d) element may be the same as in step 1 of production process (3).

There are no particular restrictions on the order of adding the group (b) compound and the group (d) element to the palladium suspension, and two or more may be added simultaneously or in any desired order. That is, a group (b) compound and a group (d) element may be added simultaneously, or a group (d) element may be added and separated prior to adding the group (b) compound.

When a metallic palladium starting compound that can be converted to metallic palladium is converted to metallic palladium in step 2, the method therefor, i.e. the reduction treatment method, is the same as in step 2 of production process (1) according to the invention (XI).

The catalyst of the invention (VIII) can be obtained in the manner described above.

Production process (4) according to the invention (XI) will now be explained. Production process (4) according to the invention (XI) is a process for production of a catalyst according to the invention (IX), and it comprises step 1 and step 2 of production process (1) according to the invention (XI), as well as step 3 in which (c) at least one element selected from the group consisting of Group 14 elements, Group 15 elements and Group 16 elements of the Periodic Table and (d) at least one element selected from the group consisting of Group 6 elements, Group 7 elements, Group 8 elements, Group 9 elements, Group 10 elements, Group 11 elements and Group 12 elements of the Periodic Table, are added in either or both of these steps.

The starting compound for the (a) metallic palladium used in step 1 of this process, and the method for its dissolution or suspension, are the same as in step 1 of production process (I) according to the invention (XI).

The starting material that gives the group (c) element, and the method for its dissolution or suspension, are the same as in step 1 of production process (2) according to the invention (XI).

The starting material that gives the group (d) element, and the method for its dissolution or suspension, are the same as in step 1 of production process (3) for a catalyst according to the invention (XI).

When a metallic palladium starting compound that can be converted to metallic palladium is converted to metallic palladium in step 1, the method therefor, i.e. the reduction treatment method, is the same as in step 1 of production process (1) according to the invention (XI).

The palladium suspension may be obtained in the manner described above.

The group (b) compound used for step 2 is the same as for the catalyst of the invention (VI), and the method of dissolving or suspending the group (b) compound and the method of removing the solvent are the same as in step 2 of production process (1) for the catalyst of the invention (VI), according to the invention (XI).

When a group (c) element is added in step 2, the starting compound for the element and the method of dissolving or suspending the starting compound for the group (c) element may be the same as in step 1 of production process (2) for the catalyst of the invention (VII), according to the invention (XI).

When a group (d) element is added in step 2, the starting compound for the element and the method of dissolving or suspending the starting compound for the group (d) element may be the same as in step 1 of production process (3) for the catalyst of the invention (VIII), according to the invention (XI).

There are no particular restrictions on the order of adding the group (b) compound and/or the group (c) element and/or the group (d) element to the palladium suspension, and three or more may be added simultaneously or in any desired order. That is, a group (b) compound, a group (c) element and a group (d) element may be added simultaneously, or a group (b) compound and a group (c) element may be added simultaneously and separated, and then another suspension containing a group (b) compound and a group (c) element may be prepared and a group (d) element added thereto.

When a metallic palladium starting compound that can be converted to metallic palladium is converted to metallic palladium in step 2, the method therefor, i.e. the reduction treatment method, is the same as in step 2 of production process (1) according to the invention (XI).

The catalyst of the invention (IX) can be obtained in the manner described above.

A process for production of a carrier-held catalyst of the invention (X) according to the invention (XII) will now be explained. The process of the invention (XII) is a process for production of a carrier-held catalyst for production of acetic acid and ethyl acetate according to the invention (X).

Production process (1) for a carrier-held catalyst of the invention (X) according to the invention (XII) comprises the following steps 1 and 2.

Step 1

A step wherein (a) metallic palladium is loaded on a carrier to obtain a metallic palladium-loaded catalyst.

Step 2

A step wherein (b) at least one compound selected from the group consisting of inorganic acids and salts thereof is loaded on the metallic palladium-loaded catalyst obtained in step 1 to obtain a catalyst for production of acetic acid and ethyl acetate.

Step 1 of production process (1) according to the invention (XII) is a step wherein metallic palladium is loaded on a carrier to obtain a metallic palladium-loaded catalyst.

The metallic palladium starting compound used in step 1 is the same as in step 1 of production process (1) according to the invention (XI).

There are no particular restrictions on the method of loading the metallic palladium, or the metallic palladium starting compound-that can be converted to metallic palladium, on the carrier, and the loading may be accomplished by any method. For example, for loading of a metallic palladium starting compound that can be converted to metallic palladium, the loading on the carrier may be accomplishing by dissolving or suspending the metallic palladium starting compound in an appropriate solvent such as water or acetone, an inorganic or organic acid such as hydrochloric acid, nitric acid, acetic acid, etc., or a mixture thereof, and then loading the solution onto the carrier and drying it. For the loading process there may be mentioned means such as the impregnation method, evaporation to dry hardness method, kneading method and spray method, but there is no limitation to these.

When a metallic palladium starting compound that can be converted to metallic palladium is loaded, the method of subsequently converting the metallic palladium starting compound to metallic palladium, i.e. the reduction treatment method, is not particularly restricted. The reduction treatment may be carried out in either a liquid phase or vapor phase state, and the conditions are not particularly restricted so long as they are common reducing conditions. Liquid phase reduction treatment is usually carried out at room temperature, but it may also be conducted with heating to a higher temperature, for example, about 30–50° C. Vapor phase reduction treatment is preferably carried out with heating of the metallic palladium starting compound-loaded carrier to about 100–600° C. in order to achieve total conversion to metallic palladium.

Specifically there may be mentioned a method whereby the metallic palladium starting compound is reduced to metallic palladium using an appropriate reducing agent such as hydrazine, formalin, hydrogen, methanol, ethylene or the like, either directly or after treatment with an aqueous solution of sodium hydroxide, potassium hydroxide, barium hydroxide, sodium metasilicate, etc. to convert the metallic palladium starting compound to an oxide, hydroxide, or the like.

The procedure for conversion to metallic palladium of the metallic palladium starting compound that can be converted to metallic palladium may be carried out after separating the catalyst holding the metallic palladium starting compound, or it may be carried out immediately following the loading procedure. If conditions permit, it is preferably carried out immediately following the loading procedure, without separation.

If desired, the metallic palladium-loaded catalyst may then be filtered by a common method and then washed and dried to remove out any reaction-inhibiting substances for the catalytic reaction, such as halides or alkali salts of sodium, etc.

The metallic palladium-loaded catalyst can be obtained in the manner described above.

Step 2 of production process (1) according to the invention (XII) is a step wherein a catalyst of the invention (X) is obtained by loading (b) at least one compound selected from the group consisting of inorganic acids and salts thereof on the metallic palladium-loaded catalyst obtained in step 1.

In step 2, the group (b) compound is the same as for the catalyst of the invention (VI). There are no particular restrictions on the method of loading the group (b) compound, and the loading may be accomplished by any publicly known method. Specifically there may be mentioned such means as the impregnation method, spray method, evaporation to dry hardness method, kneading method and adsorption method, but there is no limitation to these. The solvent used for impregnation may be any one which can dissolve the inorganic acid, and water, organic solvents and their mixtures may be used. Water, alcohol and the like are preferably used.

A catalyst of the invention (X) can be obtained in this manner.

Production process (2) for a carrier-held catalyst of the invention (X) according to the invention (XII) comprises addition of (c) at least one element selected from the group consisting of Group 14 elements, Group 15 elements and Group 16 elements of the Periodic Table, in either or both of steps 1 and 2 of production process (1) according to the invention (XII).

The starting compound for the (a) metallic palladium used in step 1 of production process (2), and the method for its loading and conversion to metallic palladium, are the same as in step 1 of production process (1) according to the invention (XII).

When a group (c) element is added in step 1, the starting compound for the group (c) element is the same as in step 1 of production process (2) according to the invention (XI).

There are no particular restrictions on the method of loading the starting compound for the group (c) element on the carrier, and the loading may be accomplished by any method. For example, the starting compound for the group (c) element may be dissolved in an appropriate solvent such as water or acetone, in an inorganic acid or organic acid such as hydrochloric acid, nitric acid, acetic acid, or the like, and then impregnated into the carrier and dried, as the method of loading onto the carrier.

The loading method may be any of such means as the impregnation method, evaporation to dry hardness method, kneading method, spray method, or the like, but there is no limitation to these.

The loading of the starting compound for the (a) metallic palladium on the carrier and the loading of the starting compound for the group (c) element on the carrier may be carried out in any order. That is, both loadings may be carried out simultaneously, or one before the other. Preferred and most common is simultaneous loading on the carrier of the starting compound for the group (c) element and the starting compound for the (a) metallic palladium on the carrier.

If desired, the metallic palladium-loaded catalyst may then be filtered by a common method and then washed and dried to remove out any reaction-inhibiting substances for the catalytic reaction, such as halides or alkali salts of sodium, etc.

The metallic palladium-loaded catalyst can be obtained in the manner described above.

Step 2 of production process (2) is a step whereby a catalyst of the invention (X) is obtained by loading (b) at least one compound selected from the group consisting of inorganic acids and salts thereof and/or (c) at least one element selected from the group consisting of Group 14 elements, Group 15 elements and Group 16 elements of the Periodic Table on the metallic palladium-loaded catalyst obtained in step 1.

In step 2, the group (b) compound and the method for its loading are the same as in step 2 of production process (1) according to the invention (XII).

When a group (c) element is loaded in step 2, the starting compound for the group (c) element and the method of its loading are the same as in step 1 of production process (2).

The loading of the group (b) compound on the metallic palladium-loaded catalyst and the loading of the starting compound for the group (c) element on the metallic palladium-loaded catalyst may be carried out in any order. That is, both loadings may be carried out simultaneously, or one before the other.

A catalyst of the invention (X) can be obtained in the manner described above.

Production process (3) for a carrier-held catalyst of the invention (X) according to the invention (XII) comprises a step of adding (d) at least one element selected from the group consisting of Group 6 elements, Group 7 elements, Group 8 elements, Group 9 elements, Group 10 elements, Group 11 elements and Group 12 elements of the Periodic Table in either or both step 1 and step 2 of production process (1) according to the invention (XII).

The starting compound for the (a) metallic palladium used in step 1 of production process (3), and the method for its loading and conversion to metallic palladium, are the same as in step 1 of production process (1) according to the invention (XII).

When a group (d) element is added in step 1, the starting compound for the group (d) element is the same as in step 1 of production process (3) according to the invention (XI).

There are no particular restrictions on the method of loading the starting compound for the group (d) element on the carrier, and any method may be employed. For example, the starting compound for the group (d) element may be dissolved in an appropriate solvent such as water or acetone, in an inorganic acid or organic acid such as hydrochloric acid, nitric acid, acetic acid, or the like, and then impregnated into the carrier and dried, as the method of loading onto the carrier.

The loading method may be any of such means as the impregnation method, evaporation to dry hardness method, kneading method, spray method, or the like, but there is no limitation to these.

The loading of the starting compound for the (a) metallic palladium on the carrier and the loading of the starting compound for the group (d) element on the carrier may be carried out in any order. That is, both loadings may be carried out simultaneously, or one before the other. Preferred and most common is simultaneous loading on the carrier of the starting compound for the group (d) element and the starting compound for the (a) metallic palladium on the carrier.

If desired, the metallic palladium-loaded catalyst may then be filtered by a common method and then washed and dried to remove out any reaction-inhibiting substances for the catalytic reaction, such as halides or alkali salts of sodium, etc.

The metallic palladium-loaded catalyst can be obtained in the manner described above.

Step 2 of production process (3) is a process whereby a catalyst of the invention (X) is obtained by loading (b) at least one compound selected from the group consisting of inorganic acids and salts thereof and/or (d) at least one element selected from the group consisting of Group 6 elements, Group 7 elements, Group 8 elements, Group 9 elements, Group 10 elements, Group 11 elements and Group 12 elements of the Periodic Table on the metallic palladium-loaded catalyst obtained in step 1.

In step 2, the group (b) compound and the method for its loading are the same as in step 2 of production process (1) according to the invention (XII).

When a group (d) element is loaded in step 2, the starting compound for the group (d) element and the method of its loading are the same as in step 1 of production process (3).

The loading of the group (b) compound on the metallic palladium-loaded catalyst and the loading of the starting compound for the group (d) element on the metallic palladium-loaded catalyst may be carried out in any order. That is, both loadings may be carried out simultaneously, or one before the other.

A catalyst of the invention (X) can be obtained in the manner described above.

Production process (4) for a carrier-held catalyst of the invention (X) according to the invention (XII) is a production process used to obtain a catalyst of the invention (IV). The catalyst of the invention (IV) allows production by adding (c) at least one element selected from the group consisting of Group 14 elements, Group 15 elements and Group 16 elements of the Periodic Table and (d) at least one element selected from the group consisting of Group 6 elements, Group 7 elements, Group 8 elements, Group 9 elements, Group 10 elements, Group 11 elements and Group 12 elements of the Periodic Table in either or both step 1 and step 2 of production process (1) according to the invention (XII).

In production process (4), the starting compound for the (a) metallic palladium used in step 1, and the method for its loading and conversion to metallic palladium, are the same as in step 1 of production process (1) according to the invention (XII).

When a group (c) element is added in step 1, the starting compound for the group (c) element and the method for its loading are the same as in step 1 of production process (2) according to the invention (XII).

When a group (d) element is added, the starting compound for the group (d) element and the method for its loading are the same as in step 1 of production process (3) according to the invention (XII).

The loading of the starting compound for the (a) metallic palladium on the carrier and the loading of the starting compound for the group (c) element and/or the starting compound for the group (d) element on the carrier may be carried out in any order. That is, all three loadings may be carried out simultaneously, or any one before the others. Preferred and most common is loading on the carrier of the starting compound for the group (c) element and the starting compound for the group (d) element simultaneously with the starting compound for the (a) metallic palladium.

If desired, the metallic palladium-loaded catalyst may then be filtered by a common method and then washed and dried to remove out any reaction-inhibiting substances for the catalytic reaction, such as halides or alkali salts of sodium, etc.

The metallic palladium-loaded catalyst can be obtained in the manner described above.

Step 2 of production process (4) is a process whereby a catalyst of the invention (X) is obtained by loading (b) at least one compound selected from the group consisting of inorganic acids and salts thereof and/or (c) at least one element selected from the group consisting of Group 14 elements, Group 15 elements and Group 16 elements of the Periodic Table and/or (d) at least one element selected from the group consisting of Group 6 elements, Group 7 elements, Group 8 elements, Group 9 elements, Group 10 elements, Group 11 elements and Group 12 elements of the Periodic Table on the metallic palladium-loaded catalyst obtained in step 1.

In step 2, the group (b) compound and the method for its loading are the same as in step 2 of production process (1) according to the invention (XII).

When a group (c) element is loaded in step 2, the starting compound for the group (c) element and the method for its loading are the same as in step 1 of production process (2) according to the invention (XII).

When a group (d) element is loaded in step 2, the starting compound for the group (d) element and the method for its loading are the same as in step 1 of production process (3) according to the invention (XII).

In step 2, the loading of the group (b) compound on the metallic palladium-loaded catalyst and/or the loading of the starting compound for the group (c) element and/or the starting compound for the group (d) element on the metallic palladium-loaded catalyst may be carried out in any order. That is, the loadings may be carried out simultaneously, or any one before the others.

A catalyst of the invention (X) can be obtained in the manner described above.

The process for production of acetic acid and ethyl acetate according to the invention (XIII) will now be explained. The invention (XIII) is a process for production of acetic acid and ethyl acetate from ethanol and oxygen using a catalyst according to any one of the inventions (VI) to (X).

The reaction process is not particularly restricted so long as it allows the catalyst of the invention to react ethanol with oxygen, and it may be any of a variety of processes including a batch process, semi-batch process, semi-continuous process, continuous flow process or a combination thereof, for a vapor phase reaction and/or liquid phase reaction.

The ethanol starting material may be supplied in liquid form, or it may be supplied in vapor form. That is, the reaction process may be, for example, a semi-continuous process whereby the catalyst of the invention is suspended in liquid ethanol and/or an ethanol solution and oxygen is passed through, or a continuous flow process whereby ethanol and oxygen gas are passed through the catalyst. A vapor phase continuous flow process if preferred from the standpoint of separation of the catalyst, starting materials and products, and the standpoint of productivity. More preferred, and advantageous in practical terms, is to employ a fixed bed having corrosion-resistant reaction tubes packed with the catalyst of the invention, for a vapor phase reaction in which the ethanol and oxygen are passed through.

A vapor phase reaction and liquid phase reaction used for production of acetic acid and ethyl acetate according to the invention (XIII) will now be explained.

A vapor phase reaction will be explained first.

There are no particular restrictions on the reaction temperature for the reaction of ethanol and oxygen in a vapor phase according to the acetic acid and ethyl acetate production method of the invention (XIII), but it is preferably 100–250° C. If the reaction temperature is below 100° C. the reaction rate may be insufficient, while if it is above 250° C. a greater number of secondary reactions will tend to occur. More preferred in practical terms is the range of 110–230° C.

In terms of the equipment, it is advantageous in practice for the reaction pressure to be from 0.0 to 3.0 MPa (gauge pressure), and more preferably in the range of 0.1 to 1.5 MPa (gauge pressure).

In the case of a flow-type reaction, the gas supplied to the reaction system comprises ethanol and oxygen, and if necessary nitrogen, carbon dioxide, a rare gas or the like may also be used as a diluent. The ethanol is supplied to the reaction system in an amount corresponding to a proportion of 0.1–50% by volume, and especially 0.5–40% by volume, and the oxygen in an amount corresponding to a proportion of 1–15% by volume, and especially 2–10% by volume, with respect to the total amount of supply gas. Here, a high concentration of ethanol in the supply gas will result in greater production of ethyl acetate, while a lower concentration will tend to result in higher selectivity for acetic acid. An ethanol concentration exceeding 50% by volume will tend to increase the number of secondary reactions, while a concentration of under 0.1% by volume will tend to lower the productivity.

The presence of water in the reaction system will provide a notable effect of improved acetic acid and ethyl acetate production activity and selectivity, as well as prolonged activity of the catalyst in the reaction system. It is suitable for water vapor to be included in the reaction gas at 0.1–50% by volume. If the water vapor in the reaction gas is present at less than 0.1% by volume the catalyst may tend to undergo deterioration more readily, and if it is present at greater than 50% by volume, the steam unit requirement may be poorer. In practical terms, the range is preferably 0.5–40% by volume.

When carrying out the process of the invention (XIII) by this gas phase reaction it is advantageous to use a high purity ethanol starting material, but there is no problem with mixing a small amount of a lower saturated hydrocarbon such as methane, ethane or propane, or acetaldehyde, diethyl ether, ethylene or the like. In particular, acetaldehyde, diethyl ether and ethylene that are trace by-products of this reaction can be converted to acetic acid and/or ethyl acetate by a catalyst of the invention. The oxygen can also be in a form such as air, diluted with an inert gas such as nitrogen, carbon dioxide gas or the like, but when the reaction gas is circulated it is generally more advantageous to use oxygen at a high concentration, preferably 99% or greater. The reaction mixture gas is preferably passed through the catalyst at a space velocity (SV) in the range of 500–15,000 hr$^{-1}$, and especially 1000–10,000 hr$^{-1}$, in a standard state.

Next, a liquid phase reaction will be explained.

There are no particular restrictions on the reaction temperature for the reaction of ethanol and oxygen in a liquid phase according to the acetic acid and ethyl acetate production method of the invention (XIII), but it is preferably 0–200° C. If the reaction temperature is below 0° C. the reaction rate may be insufficient, while if it is above 200° C. a greater-number of secondary reactions will tend to occur. More preferred in practical terms is the range of 20–110° C.

In terms of the equipment, it is advantageous in practice for the reaction pressure to be from 0.0 to 3.0 MPa (gauge pressure), and more preferably in the range of 0.1 to 1.5 MPa (gauge pressure).

The ethanol and/or oxygen starting materials may be present in the catalyst beforehand, or they may be added at an appropriate point during the reaction. When they are supplied to the reaction system, they may be in gaseous and/or liquid form. The starting material supplied to the reaction system comprises ethanol and oxygen, and if necessary nitrogen, carbon dioxide or a diluting gas may also be used.

The presence of water in the reaction system will provide a notable effect of improved acetic acid and ethyl acetate production activity and selectivity, as well as prolonged activity of the catalyst in the reaction system. The proportion of water and ethanol in the reaction system is not particularly restricted. The proportion of water and ethanol may even be changed during the reaction, or an appropriate amount of water may be added to keep a constant proportion. If desired, a basic component such as sodium hydroxide may be added to increase the reaction rate.

When carrying out the invention (XIII) by this liquid phase reaction it is advantageous to use a high purity ethanol starting material, but there is no problem with mixing a small amount of a lower saturated hydrocarbon such as methane, ethane or propane, or acetaldehyde, diethyl ether, ethylene or the like. In particular, acetaldehyde, diethyl ether and ethylene that are trace by-products of this reaction can be converted to acetic acid and/or ethyl acetate by a catalyst of the invention. The oxygen can also be in a form such as air, diluted with an inert gas such as nitrogen, carbon dioxide gas or the like, but when the reaction gas is circulated it is generally more advantageous to use oxygen at a high concentration, preferably 99% or greater.

Production of acetic acid and ethyl acetate according to the invention (XIII) in this manner allows acetic acid and ethyl acetate to be obtained with high activity and high selectivity from ethanol and oxygen. The acetic acid and ethyl acetate obtained may be separated and purified by common methods, to the desired degree of purity. When unreacted starting materials and by-products of acetaldehyde, diethyl ether and ethylene remain, those unreacted starting materials and by-products of acetaldehyde, diethyl ether and ethylene can be recovered and recycled into the reaction system for use.

When either acetic acid or ethyl acetate is required for industrial use, it may be separated and removed after the reaction to obtain the desired substance, and the other product returned to the reaction system. For example, if ethyl acetate is required, the desired ethyl acetate may be separated and recovered after the reaction and the acetic acid returned to the reaction system, to obtain additional ethyl acetate from acetic acid and ethanol.

When necessary, the catalyst used may be regenerated at an appropriate point or separated for repeated used.

The present invention will now be explained in greater detail by way of the following examples, which are only generally illustrative of the invention and are not intended to restrict it in any way.

All of the carriers used in the following examples were dried in air at 110° C. for 4 hours, as pretreatment. The water used in the examples was deionized water.

EXAMPLE 1

A silica carrier [KA-1, particle size: 5 mm$\phi$, product of Züd-chemie AG] (69 g) was added to an aqueous solution (45 ml) of sodium tetrachloropalladate [$Na_2PdCl_4$, product of Tanaka Kikinzoku] (1.90 g) and telluric acid [$H_6TeO_6$, product of Kanto Chemical Co.] (0.13 g), to absorb the entire amount. This was then added to an aqueous solution (100 ml) of sodium metasilicate nonahydrate [$Na_2SiO_3 \cdot 9H_2O$, product of Wako Junyaku] (5.5 g), and the mixture was allowed to stand at room temperature for 20 hours. After then adding hydrazine monohydrate [$N_2H_4 \cdot H_2O$, product of Wako Junyaku] (5 g) thereto and gently stirring, the mixture was allowed to stand at room temperature for 4 hours for reduction to metallic palladium. After filtering the catalyst and performing decantation, it was transferred to a glass column equipped with a stopcock and purified water was passed through for 40 hours at a rate of about 1.5 liters per hour for washing. This was then dried for 4 hours under an air stream at 110° C. to obtain acetic acid production catalyst 1.

EXAMPLE 2

Acetic acid production catalyst 2 was obtained by the same procedure as Example 1, except that lead acetate trihydrate [$(CH_3COO)_2Pb$, product of Wako Junyaku] (0.74 g) was used instead of the telluric acid in Example 1.

EXAMPLE 3

A silica carrier [KA-1, particle size: 5 mm$\phi$, product of Züd-chemie AG] (69 g) was added to an aqueous solution (45 ml) of sodium tetrachloropalladate (1.90 g), to absorb the entire amount. This was then added to an aqueous solution (100 ml) of sodium metasilicate nonahydrate (5.5 g), and the mixture was allowed to stand at room temperature for 20 hours. After then adding hydrazine monohydrate (5 g) thereto and gently stirring, the mixture was allowed to stand at room temperature for 4 hours for reduction to metallic palladium. After filtering the catalyst and performing decantation, it was transferred to a glass column equipped with a stopcock and purified water was passed through for 40 hours at a rate of about 1.5 liters per hour for washing. This was then dried for 4 hours under an air stream at 110° C. to obtain a metallic palladium-loaded catalyst.

This metallic palladium-loaded catalyst was then added to an aqueous solution (45 ml) of sodium tellurite [$Na_2TeO_3$, product of Wako Junyaku] (0.12 g) to absorb the entire amount. This was then dried for 4 hours under an air stream at 110° C. to obtain acetic acid production catalyst 3.

EXAMPLE 4

Acetic acid production catalyst 4 was obtained by the same procedure as Example 3, except that an acetic acid solution of bismuth nitrate pentahydrate [$Bi(NO_3)_2 \cdot 5H_2O$, product of Wako Junyaku] (0.37 g) was used instead of the sodium tellurite in Example 3.

EXAMPLE 5

Acetic acid production catalyst 5 was obtained by the same procedure as Example 3, except that an acetic acid solution of tin acetate [$CH_3(COO)_2Sn$, product of Wako Junyaku] (0.26 g) was used instead of the sodium tellurite in Example 3.

EXAMPLE 6

A silica carrier [CARiACT, Q-10, product of Fuji Silicia Chemical Co.] (57 g) was added to an aqueous solution (56 ml) of sodium tetrachloropalladate (1.90 g), to absorb the entire amount. This was then added to an aqueous solution (100 ml) of sodium metasilicate nonahydrate (6.0 g), and the mixture was allowed to stand at room temperature for 20 hours. After then adding hydrazine monohydrate (5 g) thereto and gently stirring, the mixture was allowed to stand at room temperature for 4 hours for reduction to metallic palladium. After filtering the catalyst and performing decantation, it was transferred to a glass column equipped with a stopcock and purified water was passed through for 40 hours at a rate of about 1.5 liters per hour for washing. This was then dried for 4 hours under an air stream at 110° C. to obtain a metallic palladium-loaded catalyst.

This metallic palladium-loaded catalyst was then added to an aqueous solution (55 ml) of sodium tellurite (0.12 g) to absorb the entire amount. This was then dried for 4 hours under an air stream at 110° C. to obtain acetic acid production catalyst 6.

EXAMPLE 7

A titania carrier [CS-300S-46, particle size: 3–5 mm$\phi$, product of Sakai Chemical Industries] (107 g) was added to an aqueous solution (42 ml) of sodium tetrachloropalladate (1.90 g), to absorb the entire amount. This was then added to an aqueous solution (100 ml) of sodium metasilicate nonahydrate (6.0 g), and the mixture was allowed to stand at room temperature for 20 hours. After then adding hydrazine monohydrate (5 g) thereto and gently stirring, the mixture was allowed to stand at room temperature for 4 hours for reduction to metallic palladium. After filtering the catalyst and performing decantation, it was transferred to a glass column equipped with a stopcock and purified water was passed through for 40 hours at a rate of about 1.5 liters per hour for washing. This was then dried for 4 hours under an air stream at 110° C. to obtain a metallic palladium-loaded catalyst.

This metallic palladium-loaded catalyst was then added to an aqueous solution (42 ml) of sodium tellurite (0.12 g) to absorb the entire amount. This was then dried for 4 hours under an air stream at 110° C. to obtain acetic acid production catalyst 7.

EXAMPLE 8

A silica carrier [KA-1, particle size: 5 mm$\phi$, product of Züd-chemie AG] (69 g) was added to an aqueous solution (45 ml) of sodium tetrachloropalladate (1.90 g) and tetrachloro aurate tetrahydrate [$H_4AuCl_4·4H_2O$, product of Tanaka Kikinzoku] (0.50 g), to absorb the entire amount. This was then added to an aqueous solution (100 ml) of sodium metasilicate nonahydrate (6.9 g), and the mixture was allowed to stand at room temperature for 20 hours. After then adding hydrazine monohydrate (6.5 g) thereto and gently stirring, the mixture was allowed to stand at room temperature for 4 hours for reduction to metallic palladium. After filtering the catalyst and performing decantation, it was transferred to a glass column equipped with a stopcock and purified water was passed through for 40 hours at a rate of about 1.5 liters per hour for washing. This was then dried for 4 hours under an air stream at 110° C. to obtain acetic acid production catalyst 8.

EXAMPLE 9

Acetic acid production catalyst 9 was obtained by the same procedure as Example 8, except that zinc chloride [$ZnCl_2$, product of Wako Junyaku] (0.08 g) was used instead of the tetrachloro aurate tetrahydrate in Example 8.

EXAMPLE 10

Acetic acid production catalyst 10 was obtained by the same procedure as Example 8, except that chromium chloride hexahydrate [$CrCl_3·6H_2O$, product of Wako Junyaku] (0.22 g) was used instead of the tetrachloro aurate tetrahydrate in Example 8.

EXAMPLE 11

Acetic acid production catalyst 11 was obtained by the same procedure as Example 8, except that manganese chloride tetrahydrate [$MnCl_2·4H_2O$, product of Wako Junyaku] (0.23 g) was used instead of the tetrachloro aurate tetrahydrate in Example 8.

EXAMPLE 12

A silica carrier [KA-1, particle size: 5 mmφ, product of Züd-chemie AG] (69 g) was added to an aqueous solution (45 ml) of sodium tetrachloropalladate (1.90 g) and tetrachloro aurate tetrahydrate (0.50 g), to absorb the entire amount. This was then added to an aqueous solution (100 ml) of sodium metasilicate nonahydrate (6.9 g), and the mixture was allowed to stand at room temperature for 20 hours. After then adding hydrazine monohydrate (6.5 g) thereto and gently stirring, the mixture was allowed to stand at room temperature for 4 hours for reduction to metallic palladium. After filtering the catalyst and performing decantation, it was transferred to a glass column equipped with a stopcock and purified water was passed through for 40 hours at a rate of about 1.5 liters per hour for washing. This was then dried for 4 hours under an air stream at 110° C. to obtain a metallic palladium-loaded catalyst containing gold.

This metallic palladium-loaded catalyst was then added to an aqueous solution (45 ml) of sodium tellurite (0.12 g), to absorb the entire amount. It was then dried for 4 hours under an air stream at 110° C. to obtain acetic acid production catalyst 12.

EXAMPLE 13

Acetic acid production catalyst 13 was obtained by the same procedure as Example 12, except that zinc chloride (0.08 g) was used instead of the tetrachloro aurate in Example 12.

EXAMPLE 14

Acetic acid production catalyst 14 was obtained by the same procedure as Example 12, except that chromium chloride hexahydrate (0.22 g) was used instead of the tetrachloro aurate in Example 12.

COMPARATIVE EXAMPLE 1

A silica carrier [KA-1, particle size: 5 mmφ, product of Züd-chemie AG) (69 g) was added to an aqueous solution (45 ml) of sodium tetrachloropalladate (1.90 g) to absorb the entire amount. This was then added to an aqueous solution (100 ml) of sodium metasilicate nonahydrate (5.5 g), and the mixture was allowed to stand at room temperature for 20 hours. After then adding hydrazine monohydrate (5 g) thereto and gently stirring, the mixture was allowed to stand at room temperature for 4 hours for reduction to metallic palladium. After filtering the catalyst and performing decantation, it was transferred to a glass column equipped with a stopcock and purified water was passed through for 40 hours at a rate of about 1.5 liters per hour for washing. This was then dried for 4 hours under an air stream at 110° C. to obtain acetic acid production catalyst 15.

Elemental Analysis of Acetic Acid Production Catalysts

Acetic acid production catalysts containing (a) palladium, a group (b) element and/or a group (c) element were subjected to heat treatment using aqua regia and/or a mixture of hydrofluoric acid and aqua regia for complete extraction of each of the components, and measurement was performed by inductively coupled plasma (ICP) emission spectroscopy. The ICP emission spectroscope used was an SPS-1700 by Seiko Denshi Kogyo, KK.

The weight ratios for each of the components in catalysts 1–15 obtained in Examples 1–14 and Comparative Example 1 and the molar ratios with respect to Pd for each of the components are shown in Table 1. The percentage values in the table represent weight percentages with respect to each catalyst.

TABLE 1

| Catalyst No. | Catalyst component (a) | Catalyst component (b) | Catalyst component (c) |
|---|---|---|---|
| Catalyst 1 | Pd 0.86% | Te (tellurium) 0.091% (Te/Pd = 0.09) | |
| Catalyst 2 | Pd 0.86% | Pb (lead) 0.54% (Pb/Pd = 0.33) | |
| Catalyst 3 | Pd 0.86% | Te (tellurium) 0.091% (Te/Pd = 0.09) | |
| Catalyst 4 | Pd 0.86% | Bi (bismuth) 0.198% (Bi/Pd = 0.12) | |
| Catalyst 5 | Pd 0.86% | Sn (tin) 0.180% (Sn/Pd = 0.19) | |
| Catalyst 6 | Pd 1.11% | Te (tellurium) 0.117% (Te/Pd = 0.09) | |
| Catalyst 7 | Pd 0.59% | Te (tellurium) 0.062% (Te/Pd = 0.09) | |
| Catalyst 8 | Pd 0.86% | | Au (gold) 0.30% (Au/Pd = 0.19) |
| Catalyst 9 | Pd 0.86% | | Zn (zinc) 0.10% (Zn/Pd = 0.10) |
| Catalyst 10 | Pd 0.86% | | Cr (chromium) 0.07% (Cr/Pd = 0.14) |

TABLE 1-continued

| Catalyst No. | Catalyst component (a) | Catalyst component (b) | Catalyst component (c) |
|---|---|---|---|
| Catalyst 11 | Pd 0.86% | | Mn (manganese) 0.088% (Mn/Pd = 0.20) |
| Catalyst 12 | Pd 0.86% | Te (tellurium) 0.091% (Te/Pd = 0.09) | Au (gold) 0.30% (Au/Pd = 0.19) |
| Catalyst 13 | Pd 0.86% | Te (tellurium) 0.091% (Te/Pd = 0.09) | Zn (zinc) 0.10% (Zn/Pd = 0.10) |
| Catalyst 14 | Pd 0.86% | Te (tellurium) 0.091% (Te/Pd = 0.09) | Cr (chromium) 0.09% (Cr/Pd = 0.15) |
| Catalyst 15 | Pd 0.86% | | |

EXAMPLES 15–28 AND COMPARATIVE EXAMPLE 2

[Production of Acetic Acid]

An SUS316 reaction tube (25 mm inner diameter) was packed with 12.5 ml of each of the acetic acid production catalysts obtained in Examples 1–14 and Comparative Example 1, and reaction was conducted with a catalyst bed reaction peak temperature of 160° C., a reaction pressure of 0.8 MPa (guage pressure), introduction of a gas supply comprising a mixture of ethanol, oxygen, steam and nitrogen at a volume ratio of 2.5:6:25:66.5 and a space velocity of 4400 hr$^{-1}$. The gas produced was cooled, and the condensed reaction solution that was collected was analyzed by gas chromatography (GC-14B, FID by Shimazu Kagaku, KK.).

The activity of each catalyst was calculated as the grams of acetic acid produced per hour per liter of catalst (space time yield, STY), and the selectivity was calculated as the percentage of product with respect to the starting ethanol.

The reaction results are shown in Table 2.

This was then added to an aqueous solution (100 ml) of sodium metasilicate nonahydrate [$Na_2SiO_3 \cdot 9H_2O$, product of Wako Junyaku] (3.8 g), and the mixture was allowed to stand at room temperature for 20 hours. After then adding hydrazine monohydrate [$N_2H_4 \cdot H_2O$] (5 g) thereto and gently stirring, the mixture was allowed to stand at room temperature for 4 hours for reduction to metallic palladium. After filtering the catalyst and performing decantation, it was transferred to a glass column equipped with a stopcock and purified water was passed through for 40 hours for washing. This was then dried for 4 hours under an air stream at 110° C. to obtain a metallic palladium-loaded catalyst.

This metallic palladium-loaded catalyst was then impregnated with an aqueous solution (45 ml) of tungstosilicic acid n-hydrate ($H_4SiW_{12}O_{40} \cdot nH_2O$: n=20–30, product of Nihon Muki Kagaku Kogyo) (44 g). The addition was performed all at once, and the mixture was gently stirred by rotation until the solution was thoroughly absorbed (about 3 minutes). After impregnation, the wet impregnated carrier was allowed to stand at room temperature for one hour. After drying in an oven for 4 hours under an air stream at 110° C., it was allowed to stand overnight in a dessicator. This produced acetic acid and ethyl acetate production catalyst 1.

EXAMPLE 30

Acetic acid and ethyl acetate production catalyst 2 was obtained by the same procedure as Example 29, except that tungstophosphoric acid n-hydrate ($H_3PW_{12}O_{40} \cdot nH_2O$: n=20–30, product of Nihon Muki Kagaku Kogyo) (59 g) was used instead of the tungstosilicic acid n-hydrate in Example 29.

EXAMPLE 31

Acetic acid and ethyl acetate production catalyst 3 was obtained by the same procedure as Example 29, except that an aqueous solution (45 ml) of manganese tungstosilicate was used instead of the tungstosilicic acid n-hydrate in Example 29.

The manganese tungstosilicate aqueous solution was obtained by dissolving manganese nitrate hexahydrate [Mn(NO$_3$)$_2$·6H$_2$O, product of Wako Junyaku] (0.38 g) in an aqueous solution of tungstosilicic acid n-hydrate (44 g).

EXAMPLE 32

Acetic acid and ethyl acetate production catalyst 4 was obtained by the same procedure as Example 29, except that

TABLE 2

| Ex. No. | Catalyst | Composition | STY acetic acid g/hlcat | Ethanol conversion rate % | Acetic acid selectivity % | Ethyl acetate % | Acet-aldehyde % | CO$_2$ % |
|---|---|---|---|---|---|---|---|---|
| Example | | | | | | | | |
| 15 | 1 | Pd—Te | 193 | 79 | 83 | 12 | 0.7 | 2.2 |
| 16 | 2 | Pd—Pb | 186 | 70 | 90 | 11 | 1.0 | 1.8 |
| 17 | 3 | Pd—Te | 198 | 80 | 84 | 11 | 1.0 | 1.8 |
| 18 | 4 | Pd—Bi | 184 | 80 | 78 | 12 | 2.3 | 5.6 |
| 19 | 5 | Pd—Sn | 163 | 73 | 76 | 12 | 2.3 | 8.6 |
| 20 | 6 | Pd—Te | 203 | 82 | 84 | 11 | 0.8 | 3.0 |
| 21 | 7 | Pd—Te | 138 | 72 | 65 | 20 | 2.0 | 8.0 |
| 22 | 8 | Pd—Au | 183 | 83 | 75 | 14 | 2.0 | 8.2 |
| 23 | 9 | Pd—Zn | 159 | 75 | 72 | 13 | 2.3 | 12.1 |
| 24 | 10 | Pd—Cr | 142 | 72 | 70 | 12 | 2.4 | 14.3 |
| 25 | 11 | Pd—Mn | 168 | 80 | 74 | 12 | 0.4 | 10.3 |
| 26 | 12 | Pd—Te—Au | 220 | 88 | 85 | 5 | 1.0 | 3.0 |
| 27 | 13 | Pd—Te—Zn | 244 | 90 | 92 | 3 | 1.4 | 3.1 |
| 28 | 14 | Pd—Te—Cr | 226 | 89 | 90 | 4 | 1.2 | 4.1 |
| Comp. Ex. | | | | | | | | |
| 2 | 15 | Pd alone | 120 | 54 | 63 | 7 | 4.5 | 25.0 |

EXAMPLE 29

A silica carrier [KA-1, particle size: 5 mmφ, product of Züd-chemie AG] (69 g) was added to an aqueous solution (45 ml) of sodium tetrachloropalladate [$Na_2PdCl_4$, product of Tanaka Kikinzoku] (1.90 g), to absorb the entire amount.

an aqueous solution (45 ml) of copper tungstosilicate was used instead of the tungstosilicic acid n-hydrate in Example 29.

The copper tungstosilicate aqueous solution was obtained by dissolving copper nitrate trihydrate [$Cu(NO_3)_2 \cdot 3H_2O$, product of Wako Junyaku] (0.32 g) in an aqueous solution of tungstosilicic acid n-hydrate (44 g).

EXAMPLE 33

A silica carrier [CARiACT, Q-15, product of Fuji Silicia Kagaku] (55 g) was added to an aqueous solution (56 ml) of sodium tetrachloropalladate (1.90 g), to absorb the entire amount. This was then added to an aqueous solution (100 ml) of sodium metasilicate nonahydrate (4.0 g), and the mixture was allowed to stand at room temperature for 20 hours. After then adding hydrazine monohydrate (5 g) thereto and gently stirring, the mixture was allowed to stand at room temperature for 4 hours for reduction to metallic palladium. After filtering the catalyst and performing decantation, it was transferred to a glass column equipped with a stopcock and purified water was passed through for 40 hours for washing. This was then dried for 4 hours under an air stream at 110° C. to obtain a metallic palladium-loaded catalyst.

This metallic palladium-loaded catalyst was then impregnated with an aqueous solution (56 ml) of tungstophosphoric acid n-hydrate ($H_3PW_{12}O_{40} \cdot nH_2O$: n=20–30, product of Nihon Muki Kagaku Kogyo) (45 g). The addition was performed all at once, and the mixture was gently stirred by rotation until the solution was thoroughly absorbed (about 3 minutes). After impregnation, the wet impregnated carrier was allowed to stand at room temperature for one hour. After drying in an oven for 4 hours under an air stream at 110° C., it was allowed to stand overnight in a dessicator. This produced acetic acid and ethyl acetate production catalyst 5.

EXAMPLE 34

A silica carrier [KA-1, particle size: 5 mmϕ, product of Züd-chemie AG] (69 g) was added to an aqueous solution (45 ml) of sodium tetrachloropalladate [$Na_2PdCl_4$, product of Tanaka Kikinzoku] (1.90 g), to absorb the entire amount. This was then added to an aqueous solution (100 ml) of sodium metasilicate nonahydrate [$Na_2SiO_3 \cdot 9H_2O$, product of Wako Junyaku] (3.8 g), and the mixture was allowed to stand at room temperature for 20 hours. After then adding hydrazine monohydrate ($N_2H_4 \cdot H_2O$) (5 g) thereto and gently stirring, the mixture was allowed to stand at room temperature for 4 hours for reduction to metallic palladium. After filtering the catalyst and performing decantation, it was transferred to a glass column equipped with a stopcock and purified water was passed through for 40 hours for washing. This was then dried for 4 hours under an air stream at 110° C. to obtain a metallic palladium-loaded catalyst.

This metallic palladium-loaded catalyst was then impregnated with an aqueous solution (45 ml) of tungstosilicic acid n-hydrate ($H_4SiW_{12}O_{40} \cdot nH_2O$: n=20–30, product of Nihon Muki Kagaku Kogyo) (44 g) and telluric acid [$H_6TeO_6$, product of Kanto Kagaku] (0.13 g). The addition was performed all at once, and the mixture was gently stirred by rotation until the solution was thoroughly absorbed (about 3 minutes). After impregnation, the wet impregnated carrier was allowed to stand at room temperature for one hour. After drying in an oven for 4 hours under an air stream at 110° C., it was allowed to stand overnight in a dessicator. This produced acetic acid and ethyl acetate production catalyst 6.

EXAMPLE 35

Acetic acid and ethyl acetate production catalyst 7 was obtained by the same procedure as Example 34, except that bismuth nitrate pentahydrate [$Bi(NO_3)_2 \cdot 5H_2O$, product of Wako Junyaku] (0.40 g) was used instead of the telluric acid in Example 34.

EXAMPLE 36

A silica carrier [KA-1, particle size: 5 mmϕ, product of Züd-chemie AG] (69 g) was added to an aqueous solution (45 ml) of sodium tetrachloropalladate (1.90 g) and tetrachloro aurate tetrahydrate [$H_4AuCl_4 \cdot 4H_2O$, product of Tanaka Kikinzoku] (0.50 g), to absorb the entire amount. This was then added to an aqueous solution (100 ml) of sodium metasilicate nonahydrate (5.2 g), and the mixture was allowed to stand at room temperature for 20 hours. After then adding hydrazine monohydrate (6.5 g) thereto and gently stirring, the mixture was allowed to stand at room temperature for 4 hours for reduction to metallic palladium. After filtering the catalyst and performing decantation, it was transferred to a glass column equipped with a stopcock and purified water was passed through for 40 hours for washing. This was then dried for 4 hours under an air stream at 110° C. to obtain a metallic palladium-loaded catalyst.

This metallic palladium-loaded catalyst was then impregnated with an aqueous solution (45 ml) of tungstosilicic acid n-hydrate ($H_4SiW_{12}O_{40} \cdot nH_2O$: n=20–30, product of Nihon Muki Kagaku Kogyo) (44 g). The addition was performed all at once, and the mixture was gently stirred by rotation until the solution was thoroughly absorbed (about 3 minutes). After impregnation, the wet impregnated carrier was allowed to stand at room temperature for one hour. After drying in an oven for 4 hours under an air stream at 110° C., it was allowed to stand overnight in a dessicator. This produced acetic acid and ethyl acetate production catalyst 8.

EXAMPLE 37

Acetic acid and ethyl acetate production catalyst 9 was obtained by the same procedure as Example 36, except that zinc chloride [$ZnCl_2$, product of Wako Junyaku] (0.08 g) was used instead of the tetrachloro aurate tetrahydrate in Example 36.

EXAMPLE 38

A silica carrier [KA-1, particle size: 5 mmϕ, product of Züd-chemie AG] (69 g) was added to an aqueous solution (45 ml) of sodium tetrachloropalladate (3.80 g) and zinc chloride (0.14 g), to absorb the entire amount. This was then added to an aqueous solution (100 ml) of sodium metasilicate nonahydrate (8.1 g), and the mixture was allowed to stand at room temperature for 20 hours. After then adding hydrazine monohydrate (6.5 g) thereto and gently stirring, the mixture was allowed to stand at room temperature for 4 hours for reduction to metallic palladium. After filtering the catalyst and performing decantation, it was transferred to a glass column equipped with a stopcock and purified water was passed through for 40 hours for washing. This was then dried for 4 hours under an air stream at 110° C. to obtain a metallic palladium-loaded catalyst containing zinc.

This metallic palladium-loaded catalyst was then added to an aqueous solution (45 ml) of sodium tellurite (0.27 g), to absorb the entire amount. It was then dried for 4 hours under an air stream at 110° C. to obtain a metallic palladium-loaded catalyst containing tellurium and zinc.

This metallic palladium-loaded catalyst was then impregnated with an aqueous solution (45 ml) of tungstosilicic acid n-hydrate ($H_4SiW_{12}O_{40} \cdot nH_2O$: n=20–30, product of Nihon Muki Kagaku Kogyo) (24 g). The addition was performed all at once, and the mixture was gently stirred by rotation until the solution was thoroughly absorbed (about 3 minutes). After impregnation, the wet impregnated carrier was allowed to stand at room temperature for one hour. After drying in an oven for 4 hours under an air stream at 110° C., it was allowed to stand overnight in a dessicator. This produced acetic acid and ethyl acetate production catalyst 10.

EXAMPLE 39

A silica carrier [KA-1, particle size: 5 mmφ, product of Z üd-chemie AG] (69 g) was added to an aqueous solution (45 ml) of sodium tetrachloropalladate (2.76 g) and tetrachloro aurate tetrahydrate (0.78 g), to absorb the entire amount. This was then added to an aqueous solution (100 ml) of sodium metasilicate nonahydrate (8.3 g), and the mixture was allowed to stand at room temperature for 20 hours. After then adding hydrazine monohydrate (6.5 g) thereto and gently stirring, the mixture was allowed to stand at room temperature for 4 hours for reduction to metallic palladium. After filtering the catalyst and performing decantation, it was transferred to a glass column equipped with a stopcock and purified water was passed through for 40 hours for washing. This was then dried for 4 hours under an air stream at 110° C. to obtain a metallic palladium-loaded catalyst containing gold.

This gold-containing metallic palladium-loaded catalyst was then impregnated with an aqueous solution (45 ml) of tungstosilicic acid n-hydrate ($H_4SiW_{12}O_{40} \cdot nH_2O$: n=20–30, product of Nihon Muki Kagaku Kogyo) (24 g) and telluric acid (0.28 g). The addition was performed all at once, and the mixture was slowly stirred by rotation until the solution was thoroughly absorbed (about 3 minutes). After impregnation, the wet impregnated carrier was allowed to stand at room temperature for one hour. After drying in an oven for 4 hours under an air stream at 110° C., it was allowed to stand overnight in a dessicator. This produced acetic acid and ethyl acetate production catalyst 11.

EXAMPLE 40

Tungstophosphoric acid n-hydrate ($H_3PW_{12}O_{40} \cdot nH_2O$: n=20–30, product of Nihon Muki Kagaku Kogyo) (150 g) was dissolved in water (75 ml) to obtain a tungstophosphoric acid aqueous solution. An aqueous solution (160 ml) of cesium nitrate [$CsNO_3$, product of Wako Junyaku] (25 g) was added dropwise over 5 minutes using a dropping funnel while vigorously stirring the tungstophosphoric acid aqueous solution, to obtain a cesium tungstophosphate slurry-like precipitate. The slurry-like precipitate was vigorously stirred while an acetone solution (10 ml) of palladium acetate [$Pd(OAc)_2$] (11.7 g) was added dropwise over 5 minutes using a dropping funnel, and then the mixture was stirred for one hour. The solvent was then effluxed off with a rotary evaporator, the precipitate was removed, and this precipitate was dried for 3 hours in an oven under an air stream at 150° C. The resulting palladium-containing cesium tungstophosphate salt was pulverized to a particle size of 3–5 mm, dried for 3 hours under an air stream at 200° C. and subjected to 5 hours of reduction treatment by a hydrogen stream at 250° C., to obtain acetic acid and ethyl acetate production catalyst 12

COMPARATIVE EXAMPLE 3

A silica carrier [KA-1, particle size: 5 mmφ, product of Z üd-chemie AG] (69 g) was added to an aqueous solution (45 ml) of sodium tetrachloropalladate (1.90 g), to absorb the entire amount. This was then added to an aqueous solution (100 ml) of sodium metasilicate nonahydrate (5.5 g), and the mixture was allowed to stand at room temperature for 20 hours. After then adding hydrazine monohydrate (5 g) thereto and gently stirring, the mixture was allowed to stand at room temperature for 4 hours for reduction to metallic palladium. After filtering the catalyst and performing decantation, it was transferred to a glass column equipped with a stopcock and purified water was passed through for 40 hours for washing. This was then dried for 4 hours under an air stream at 110° C. to obtain acetic acid and ethyl acetate production catalyst 13.

COMPARATIVE EXAMPLE 4

A γ-alumina carrier [NST-3, particle size: 3.2 mmφ, product of Nikki Universal] (50 g) was added to an aqueous solution (30 ml) of sodium tetrachloropalladate (1.90 g), to absorb the entire amount. This was then added to an aqueous solution (100 ml) of sodium metasilicate nonahydrate (5.5 g), and the mixture was allowed to stand at room temperature for 20 hours. After then adding hydrazine monohydrate (5 g) thereto and gently stirring, the mixture was allowed to stand at room temperature for 4 hours for reduction to metallic palladium. After filtering the catalyst and performing decantation, it was transferred to a glass column equipped with a stopcock and purified water was passed through for 40 hours for washing. This was then dried for 4 hours under an air stream at 110° C. to obtain acetic acid and ethyl acetate production catalyst 14.

Elemental Analysis of Acetic Acid and Ethyl Acetate Production Catalysts

Catalysts containing (a) metallic palladium, (b) an inorganic acid and/or salt thereof and/or a group (c) element and/or a group (d) element were subjected to heat treatment using aqua regia and/or a mixture of hydrofluoric acid and aqua regia for complete extraction of each of the components, and measurement was performed by inductively coupled plasma (ICP) emission spectroscopy. The ICP emission spectroscope used was an SPS-1700 by Seiko Denshi Kogyo, KK.

The weight ratios for each of the components in acetic acid and ethyl acetate production catalysts 1 to 14 obtained in Examples 29–40 and Comparative Examples 3 and 4 are shown in Table 3. The percentage values in the tables represent weight percentages with respect to each catalyst. The weight percentages of the heteropoly acids are expressed in terms of the values calculated for the molecular weight of each corresponding anhydride. For the group (c) elements and the group (d) elements in Table 3, the molar ratios of each element with respect to elemental Pd are shown in parentheses.

TABLE 3

| Production catalyst | Catalyst component (a) | Catalyst component (b) | Catalyst component (c) | Catalyst component (d) |
|---|---|---|---|---|
| Catalyst 1 | Pd 0.58% | tungstosilicic acid ($H_4SiW_{12}O_{40}$) 32.2% | — | — |
| Catalyst 2 | Pd 0.60% | tungstophosphoric acid ($H_3PW_{12}O_{40}$) 33.8% | — | — |
| Catalyst 3 | Pd 0.58% | manganese salt of tungstosilicic acid 33.0% ($Mn_{0.1}H_{3.6}SiW_{12}O_{40}$) | — | — |
| Catalyst 4 | Pd 0.60% | copper salt of tungstosilicic acid ($Cu_{0.1}H_{2.8}PW_{12}O_{40}$) 34.3% | — | — |
| Catalyst 5 | Pd 0.63% | tungstosilicic acid ($H_4SiW_{12}O_{40}$) 42.2% | — | — |
| Catalyst 6 | Pd 0.57% | tungstosilicic acid ($H_4SiW_{12}O_{40}$) 33.0% | Te (tellurium) 0.11% (Te/Pd = 0.09) | — |

TABLE 3-continued

| Production catalyst | Catalyst component (a) | Catalyst component (b) | Catalyst component (c) | Catalyst component (d) |
|---|---|---|---|---|
| Catalyst 7 | Pd 0.57% | tungstosilicic acid ($H_4SiW_{12}O_{40}$) 33.3% | Bi (bismuth) 0.23% (Bi/Pd = 0.12) | — |
| Catalyst 8 | Pd 0.57% | tungstosilicic acid ($H_4SiW_{12}O_{40}$) 32.1% | — | Au (gold) 0.20% (Au/Pd = 0.19) |
| Catalyst 9 | Pd 0.57% | tungstosilicic acid ($H_4SiW_{12}O_{40}$) 31.8% | — | Zn (zinc) 0.03% (Zn/Pd = 0.10) |
| Catalyst 10 | Pd 1.46% | tungstosilicic acid ($H_4SiW_{12}O_{40}$) 22.4% | Te (tellurium) 0.062% (Te/Pd = 0.09) | Zn (zinc) 0.10% (Zn/Pd = 0.10) |

EXAMPLES 41–52 AND COMPARATIVE EXAMPLES 5 AND 6

[Production of Acetic Acid and Ethyl Acetate]

An SUS316 reaction tube (25 mm inner diameter) was packed with 25.0 ml of each of the acetic acid and ethyl acetate production catalysts obtained in Examples 29–40 and Comparative Examples 3 and 4, and reaction was conducted with a catalyst bed reaction peak temperature of 160° C., a reaction pressure of 0.8 MPa (guage pressure), introduction of a gas supply comprising a mixture of ethanol, oxygen, steam and nitrogen at a volume ration of 10:6:25:59 and a space velocity of 1800 $hr^{-1}$. The gas produced was cooled, and the condensed reaction solution that was collected and its gas components were analyzed by gas chromatography (GC-14B by Shimazu Kagaku, KK., FID and TCD).

The activity of each catalyst was calculated as the grams of acetic acid and ethyl acetate produced per hour per liter of catalyst (space time yield, STY/unit g/h•lcat), and the selectivity was calculated as the percentage of product with respect to the starting ethanol.

The reaction results are shown in Table 4.

TABLE 4

| | | STY (g/h · lcat) | | Conversion rate | Selectivity (%) | | | | | |
|---|---|---|---|---|---|---|---|---|---|---|
| Ex. No. | Production catalyst | Ethyl acetate | Acetic acid | % Ethanol | Ethyl acetate | Acetic acid | $CO_2$* | Acet-aldehyde | Diethyl ether | Ethylene |
| Ex. | | | | | | | | | | |
| 41 | 1 | 172 | 45 | 63 | 78 | 15 | 2.3 | 3.3 | 1.7 | 0.2 |
| 42 | 2 | 177 | 50 | 65 | 77 | 16 | 3.5 | 2.1 | 1.0 | 0.2 |
| 43 | 3 | 170 | 53 | 65 | 74 | 17 | 3.0 | 3.2 | 2.0 | 0.2 |
| 44 | 4 | 170 | 16 | 60 | 80 | 11 | 2.9 | 3.2 | 2.0 | 0.2 |
| 45 | 5 | 182 | 38 | 66 | 78 | 12 | 3.3 | 3.5 | 1.5 | 0.5 |
| 46 | 6 | 121 | 25 | 51 | 67 | 10 | 0.7 | 4.4 | 13.0 | 1.8 |
| 47 | 7 | 124 | 29 | 50 | 70 | 12 | 1.0 | 3.1 | 13.0 | 1.0 |
| 48 | 8 | 193 | 47 | 70 | 78 | 14 | 2.0 | 1.3 | 1.6 | 1.5 |
| 49 | 9 | 212 | 43 | 75 | 80 | 12 | 2.3 | 2.8 | 1.5 | 0.5 |
| 50 | 10 | 177 | 121 | 81 | 62 | 31 | 1.3 | 0.4 | 1.1 | 4.2 |
| 51 | 11 | 189 | 119 | 85 | 63 | 28 | 1.2 | 0.4 | 1.0 | 3.8 |
| 52 | 12 | 69 | 66 | 40 | 49 | 34 | 5.3 | 5.3 | 2.3 | 3.3 |
| Comp. Ex. | | | | | | | | | | |
| 5 | 13 | 30 | 108 | 49 | 21 | 56 | 15 | 8.0 | 0.0 | 0.3 |
| 6 | 14 | 42 | 32 | 30 | 40 | 22 | 20 | 10.2 | 6.0 | 2.3 |

*$CO_2$: carbon dioxide

TABLE 3-continued

| Production catalyst | Catalyst component (a) | Catalyst component (b) | Catalyst component (c) | Catalyst component (d) |
|---|---|---|---|---|
| Catalyst 11 | Pd 1.06% | tungstosilicic acid ($H_4SiW_{12}O_{40}$) 24.4% | Te (tellurium) 0.063% (Te/Pd = 0.11) | Au (gold) 0.40% (Au/Pd = 0.19) |
| Catalyst 12 | Pd 8.6% | cesium salt of tungstophosphoric acid 96.0% ($Cs_{2.5}H_{3.5}PW_{12}O_{40}$) | — | — |
| Catalyst 13 | Pd 0.58% | — | — | — |
| Catalyst 14 | Pd 1.10% | — | — | — |

EXAMPLE 53–56

[Production of Acetic Acid and Ethyl Acetate]

An SUS316 reaction tube (25 mm inner diameter) was packed with acid and ethyl acetate production catalysts 10 obtained in Example 38 (25.0 ml), and reaction was conducted with a catalyst bed reaction peak temperature of 160° C., a reaction pressure of 0.8 MPa (gauge pressure), introduction of a gas supply comprising a mixture of ethanol, oxygen, steam and nitrogen at a volume ratio of (%) of X:6:25:(69-X) and a space velocity of 1800 $^{-1}$. The ethanol gas concentrations (X %) are shown in Table 5.

The gas produced was cooled, and the condensed reaction solution that was collected and its gas components were analyzed by gas chromatography (GC-14B by FID and TCD by Shimazu Kagaku, KK.).

The activity of each catalyst was calculated as the grams of acetic acid and ethyl acetate produced per hour per liter of catalyst (space time yield, STY), and the selectivity was calculated as the percentage of product with respect to the starting ethanol.

The reaction results are shown in Table 5.

TABLE 5

| Example No. | Ethanol gas concentration (%) | STY (g/h · lcat) Ethyl acetate | Acetic acid | Conversion rate (%) Ethanol | Selectivity (%) Ethyl acetate | Acetic acid | $CO_2$* | Acet- aldehyde | Diethyl ether | Ethylene |
|---|---|---|---|---|---|---|---|---|---|---|
| 53 | 2.5 | 5 | 104 | 98 | 6 | 92 | 2.2 | 0.1 | 0.0 | 0.0 |
| 54 | 5.0 | 46 | 175 | 93 | 26 | 72 | 2.0 | 0.3 | 0.3 | 0.0 |
| 55 | 10 | 157 | 120 | 81 | 62 | 31 | 1.3 | 0.4 | 1.1 | 4.2 |
| 56 | 15 | 279 | 75 | 70 | 72 | 14 | 0.6 | 0.4 | 5.5 | 7.2 |

*$CO_2$: carbon dioxide

INDUSTRIAL APPLICABILITY3

As explained above, by using an acetic acid production catalyst that contains (b) at least one element selected from the group consisting of Group 14 elements, Group 15 elements and Group 16 elements of the Periodic Table and/or (c) at least one element selected from the group consisting of Group 6 elements, Group 7 elements, Group 8 elements, Group 9 elements, Group 10 elements, Group 11 elements and Group 12 elements of the Periodic Table, added to a metallic palladium-loaded catalyst to prepare a catalyst for obtaining acetic acid from ethanol and oxygen, it is possible to achieve production of acetic acid with higher space time yields, lower selectivity for carbon dioxide and acetaldehyde and minimal deterioration, and therefore at higher production efficiency, compared to catalysts of the prior art.

Moreover, by using an acetic acid and ethyl acetate production catalyst that contains (b) at least one compound selected from the group consisting of inorganic acids and salts thereof and/or (c) at least one element selected from the group consisting of Group 14 elements, Group 15 elements and Group 16 elements of the Periodic Table and/or (d) at least one element selected from the group consisting of Group 6 elements, Group 7 elements, Group 8 elements, Group 9 elements, Group 10 elements, Group 11 elements and Group 12 elements of the Periodic Table, added to a metallic palladium catalyst to prepare a catalyst for obtaining acetic acid and ethyl acetate from ethanol and oxygen, it is possible to achieve production of acetic acid and ethyl acetate with higher space time yields, lower selectivity for carbon dioxide and acetaldehyde and minimal deterioration, and therefore at higher production efficiency, compared to catalysts of the prior art.

What is claimed is:

1. A catalyst for production of acetic acid and ethyl acetate by reaction of ethanol and oxygen, comprising (a) palladium and (b) at least one compound selected from the group consisting of heteropoly acids and salts thereof.

2. A process for production of a catalyst for production of acetic acid and ethyl acetate according to claim 1, which comprises the following steps 1 and 2:

Step 1

A step wherein (a) metallic palladium is loaded on a carrier to obtain a metallic palladium-loaded catalyst;

Step 2

A step wherein (b) at least one compound selected from the group consisting of heteropoly acids and salts thereof is loaded on the metallic palladium-loaded catalyst obtained in step 1 to obtain a catalyst for production of acetic acid and ethyl acetate.

3. A catalyst according to claim 1, wherein the (a) palladium is metallic palladium.

4. A catalyst according to claim 1, wherein the heteropoly acids are selected from tungstosilicic acid, tungstophosphoric acid, molybdosilicic acid, molybdophosphoric acid, vanadotungstosilicic acid, vanadotungstophosphoric acid, vanadomolybdosilicic acid and vanadomolybdophosphoric acid.

5. A catalyst according to claim 1, wherein the catalyst components are held on a carrier.

6. A catalyst according to claim 5, wherein the carrier is silica.

7. A catalyst according to claim 1, wherein the compositional ratio of (a) to (b) is (a) 1 gram: (b) 0.025–500 grams.

8. A process according to claim 2, wherein the carrier is silica.

* * * * *